United States Patent
Green et al.

(10) Patent No.: US 9,271,855 B2
(45) Date of Patent: Mar. 1, 2016

(54) CATHETER HAVING HYDRAULIC ACTUATOR WITH TANDEM CHAMBERS

(75) Inventors: Michael L. Green, Pleasanton, CA (US); Michael R. Bialas, Wildomar, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 967 days.

(21) Appl. No.: 13/467,715

(22) Filed: May 9, 2012

(65) Prior Publication Data

US 2013/0304181 A1   Nov. 14, 2013

(51) Int. Cl.
*A61F 2/06* (2013.01)
*A61F 2/966* (2013.01)

(52) U.S. Cl.
CPC ..................................... *A61F 2/966* (2013.01)

(58) Field of Classification Search
CPC ........... A61F 2/95; A61F 2/962; A61F 2/966; A61F 2002/9517; A61F 2002/958; A61F 2002/011; A61F 2002/9528; A61F 2002/9534; A61M 25/0119; A61M 25/0122; A61M 25/0155; A61M 25/1018; A61M 25/0015; A61M 25/0029; A61M 2025/1059; A61M 2025/1072; A61M 2025/1065; A61M 2025/0024; A61M 2025/0064; A61M 2025/0006; A61M 2025/0039; A61M 2025/004; A61M 2025/0175
See application file for complete search history.

(56) References Cited

U.S. PATENT DOCUMENTS

| | | | |
|---|---|---|---|
| 5,817,101 A | 10/1988 | Fiedler | |
| 5,695,468 A | 12/1997 | Lafontaine et al. | |
| 5,709,703 A | 1/1998 | Lukic et al. | |
| 5,776,141 A | 7/1998 | Klein et al. | |
| 6,056,759 A | 5/2000 | Fiedler | |
| 6,113,608 A | 9/2000 | Monroe et al. | |
| 6,214,037 B1 | 4/2001 | Mitchell et al. | |
| 6,287,285 B1 | 9/2001 | Michal et al. | |
| 6,425,898 B1 | 7/2002 | Wilson et al. | |
| 6,514,261 B1 * | 2/2003 | Randall ..................... | A61F 2/95 604/528 |
| 6,541,116 B2 | 4/2003 | Michal et al. | |
| 6,605,109 B2 | 8/2003 | Fiedler | |

(Continued)

FOREIGN PATENT DOCUMENTS

EP   1208816 A2   5/2002

OTHER PUBLICATIONS

U.S. Appl. No. 14/767,968, filed Aug. 14, 2015.
U.S. Appl. No. 14/653,582, filed Jun. 18, 2015.
U.S. Appl. No. 13/801,588, filed Jul. 9, 2015 Restriction Requirement Filed.
U.S. Appl. No. 13/801,588, filed Aug. 20, 2015 Non-Final Office Action.

(Continued)

*Primary Examiner* — Darwin Erezo
*Assistant Examiner* — Kendra Obu
(74) *Attorney, Agent, or Firm* — Baker Botts L.L.P.

(57) ABSTRACT

Catheter including an inner tubular member having a fluid lumen defined therein and an exterior surface. The exterior surface defining a first distal flow port and a second distal flow port. An outer tubular member is movable relative to the inner tubular member in a proximal direction and having an interior surface. A first pressure chamber is defined between the exterior surface and the interior surface, and between a first distal seal assembly and a first proximal seal assembly. A second pressure chamber is defined between the exterior surface and the interior surface, and between a second distal seal assembly and a second proximal seal assembly. Fluid introduced through the fluid lumen pressurizes the first pressure chamber and the second pressure chamber to generate a respective force at the first proximal seal assembly and to the second proximal seal assembly to urge the outer tubular member in the proximal direction.

33 Claims, 11 Drawing Sheets

(56) References Cited

U.S. PATENT DOCUMENTS

| | | | |
|---|---|---|---|
| 6,884,257 B1 | 4/2005 | Cox | |
| 6,945,989 B1 | 9/2005 | Betelia et al. | |
| 7,632,296 B2 * | 12/2009 | Malewicz | A61F 2/966 623/1.11 |
| 7,740,652 B2 | 6/2010 | Gerdts et al. | |
| 7,799,065 B2 | 9/2010 | Pappas | |
| 7,875,067 B2 * | 1/2011 | Von Oepen | A61F 2/958 623/1.11 |
| 8,118,853 B2 * | 2/2012 | Grewe | A61F 2/95 623/1.11 |
| 8,435,279 B2 | 5/2013 | Beyerlein et al. | |
| 8,685,076 B2 | 4/2014 | Gerdts et al. | |
| 9,119,742 B2 * | 9/2015 | Chuter | A61F 2/95 |
| 2002/0009535 A1 | 1/2002 | Michal et al. | |
| 2002/0045929 A1 | 4/2002 | Diaz | |
| 2002/0058951 A1 | 5/2002 | Fiedler | |
| 2004/0193178 A1 | 9/2004 | Nikolchev | |
| 2004/0193243 A1 | 9/2004 | Mangiardi et al. | |
| 2006/0030923 A1 * | 2/2006 | Gunderson | A61F 2/966 623/1.11 |
| 2007/0078506 A1 | 4/2007 | McCormick et al. | |
| 2007/0100413 A1 * | 5/2007 | Dwyer | A61F 2/95 623/1.11 |
| 2007/0123971 A1 | 5/2007 | Kennedy et al. | |
| 2008/0294230 A1 | 11/2008 | Parker | |
| 2009/0018529 A1 | 1/2009 | Hoffman et al. | |
| 2009/0292262 A1 | 11/2009 | Adams et al. | |
| 2009/0312832 A1 | 12/2009 | Delap | |
| 2011/0307049 A1 | 12/2011 | Kao | |
| 2013/0073024 A1 | 3/2013 | Russo et al. | |
| 2013/0297011 A1 | 11/2013 | Morris et al. | |
| 2014/0194969 A1 | 7/2014 | Headley | |
| 2014/0214151 A1 | 7/2014 | Ibeling | |

OTHER PUBLICATIONS

U.S. Appl. No. 13/797,636, filed Jun. 30, 2015 Non-Final Office Action.
U.S. Appl. No. 13/797,636, filed Oct. 30, 2015 Response to Non-Final Office Action.
CN Office Action issued Jun. 30, 2015 in CN Patent Application No. 201380007953.4.
U.S. Appl. No. 13/467,679, filed Aug. 22, 2014 Restriction Requirement.
U.S. Appl. No. 13/467,660, filed Jul. 17, 2014 Final Office Action.
U.S. Appl. No. 13/467,660, filed Jan. 4, 2014 Response to Non-Final Office Action.
International Search Report and Written Opinion for PCT/US2013/069477, dated Jan. 8, 2014.
International Search Report for PCT/US2013/068306, dated Jan. 8, 2014.
International Search Report for PCT/US2013/030830, dated Jan. 15, 2014.
International Search Report and Written Opinion for PCT/US2013/036881, dated Aug. 2, 2013.
International Search Report and Written Opinion for PCT/US2013/036884, dated Aug. 2, 2013.
International Search Report and Written Opinion for PCT/US2013/030513, dated Aug. 2, 2013.
U.S. Appl. No. 13/467,660, filed Oct. 7, 2013 Non-Final Office Action Examiner.
U.S. Appl. No. 13/467,660, filed May 9, 2012.
U.S. Appl. No. 13/467,679, filed May 9, 2012.
U.S. Appl. No. 13/797,636, filed Mar. 12, 2013.
U.S. Appl. No. 13/801,588, filed Mar. 13, 2013.

* cited by examiner

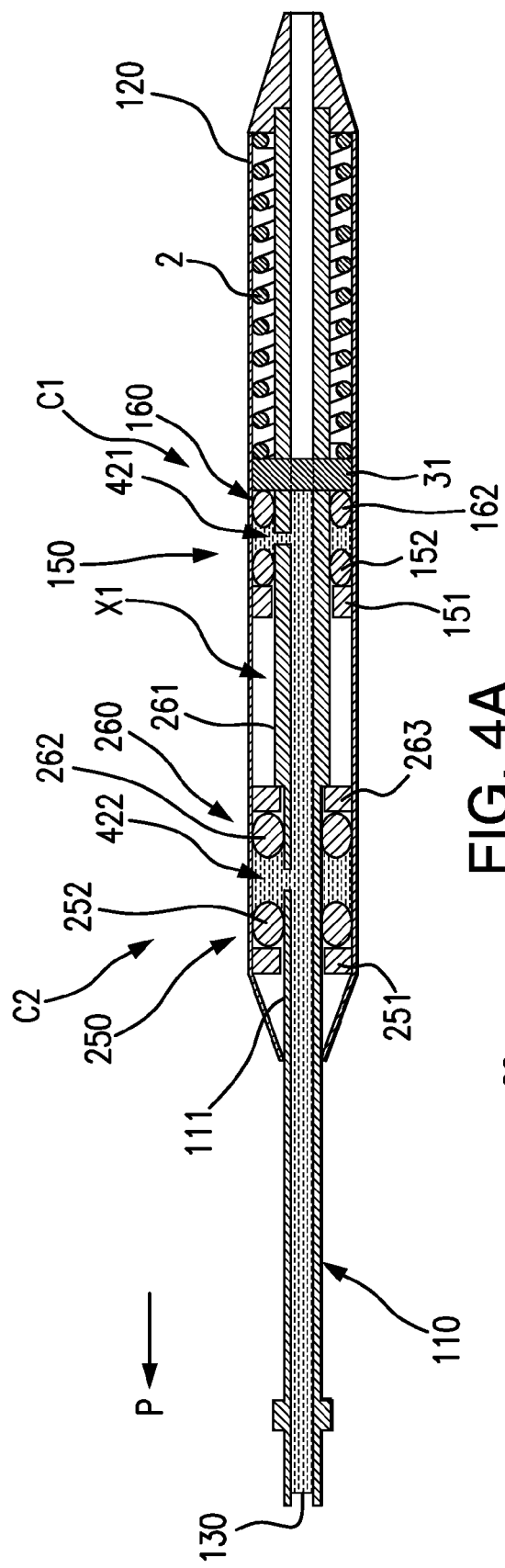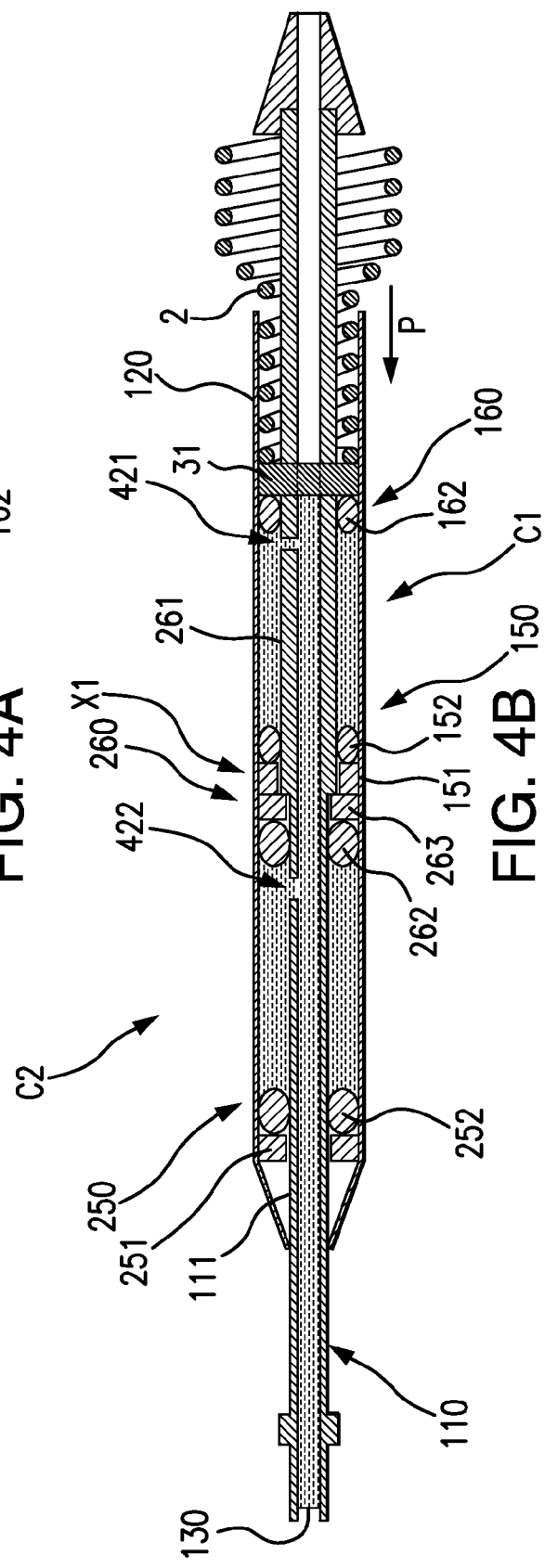

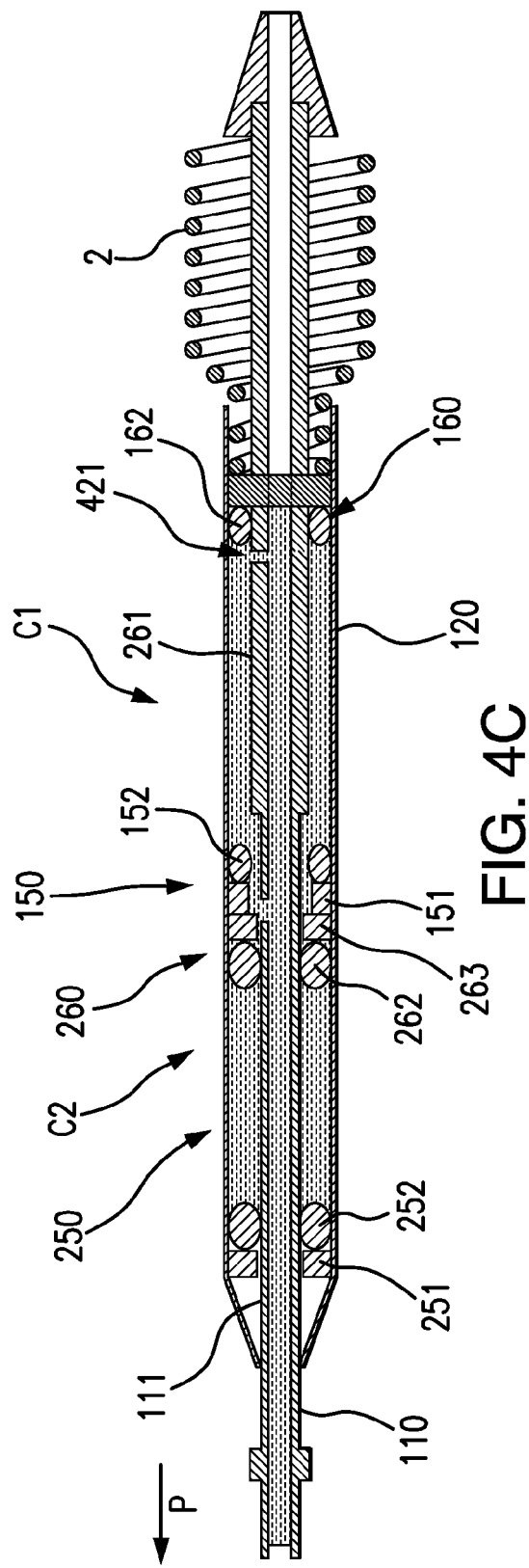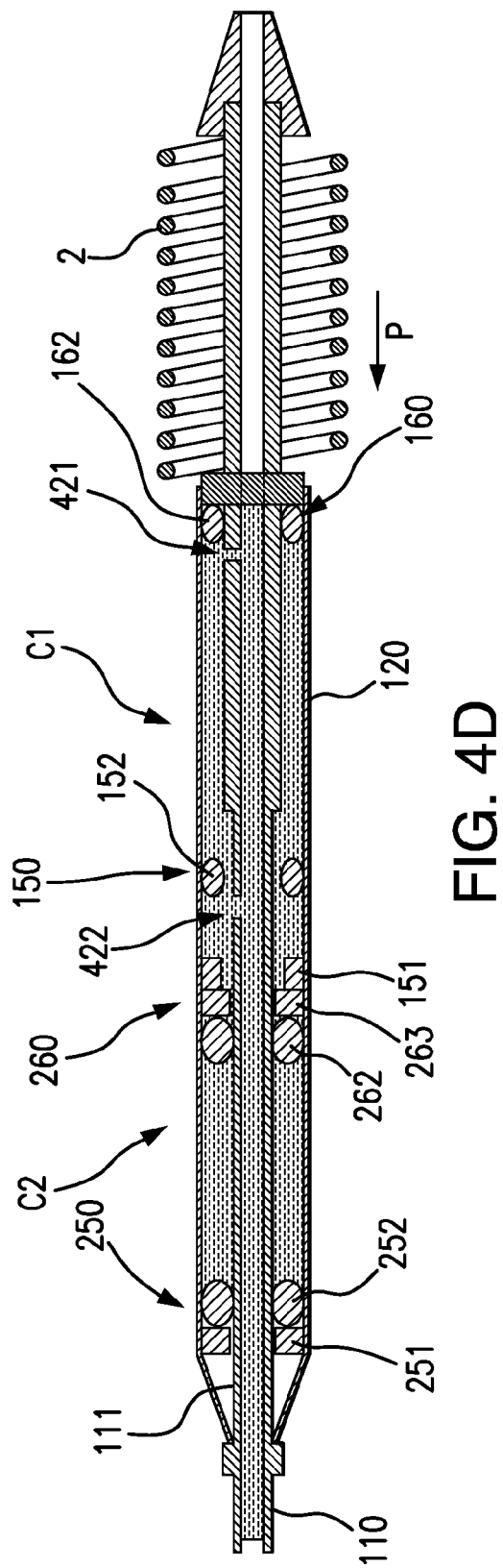

CATHETER HAVING HYDRAULIC ACTUATOR WITH TANDEM CHAMBERS

BACKGROUND OF THE DISCLOSED SUBJECT MATTER

1. Field of the Disclosed Subject Matter

The disclosed subject matter relates to catheters used in the delivery of a medical device, such as a self-expanding stent, for treating the luminal systems of a patient. Specifically, the disclosed subject matter relates to a delivery catheter having a retractable sheath moved by hydraulic chambers.

2. Description of the Related Art

A variety of systems using a retractable sheath are known for intraluminal delivery of a medical device, such as a stent or filter. However, there remains a need for continued improvement of such known delivery systems.

An example of such a delivery system is described in U.S. Pat. No. 6,425,898 to Wilson et al., which is incorporated by reference herein, wherein a delivery system is provided having an inner member with a stop attached to the inner member. During deployment, the stop prevents the stent from migrating proximally during retraction of the sheath for stent deployment.

Conventional self-expanding stent delivery systems generally comprise a handle portion and an elongated shaft, wherein the stent is disposed within a delivery portion at the distal end of the shaft. To deploy the stent, an outer sheath is provided which can be retracted relative to the stent to release the stent from its delivery configuration. The sheath in such systems generally spans the full length of the catheter resulting in an increased profile and stiffness over the entire length of the catheter. Further, because the sheath spans the full length of the catheter there is an increased risk of the sheath binding with other components of the catheter during passage through the tortuous luminal system of a patient, thus inhibiting the deployment of the stent.

Another issue with such delivery systems is that the sheath is generally pulled back in a 1-to-1 ratio with the user's input (force). Because the stent may embed in the outer sheath during storage and shipping, and due to larger static friction forces, a large amount of initial input is typically required to release the stent which may lead to incorrect placement. When initially releasing the stent, it may be desirable to slowly pull back the sheath for proper placement and then more readily retract the sheath to prevent inadvertent movement of the stent.

Further, the amount of force that is required to retract the sheath, particularly for stents of greater length as required for peripheral indications, can be substantial. Therefore there is a need for an improved delivery system for self-expanding stents having reduced force requirements for delivery of a medical device.

There thus remains a continued need for an efficient and economic system for delivering a medical device that is easy to use and provides accurate stent placement. The presently disclosed subject matter satisfies these and other needs.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

When a hydraulic system to deploy a stent is used, the resulting force applied to retract the outer tubular member generally is a function of pressure and area. However, the outer tubular member of a hydraulic cylinder can require a greater retraction force initially for retraction. Thus, under certain circumstances, it may not be desirable to continue the higher retraction force throughout the entire stroke or movement of the outer tubular member. Hence a tandem chamber catheter is disclosed herein to allow redistribution of retraction force, such that a higher retraction force can be generated initially followed by a lower retraction force during deployment.

To achieve these and other advantages and in accordance with the purpose of the disclosed subject matter, as embodied and broadly described, the disclosed subject matter includes a catheter comprising an inner tubular member having a length, an exterior surface and a fluid lumen defined therein. The exterior surface defines a first distal flow port in fluid communication with the fluid lumen and a second distal flow port located proximal to the first distal flow port in fluid communication with the fluid lumen. The catheter further includes an outer tubular member movable relative to the inner tubular member in a proximal direction along a length of the inner tubular member. The outer tubular member has an interior surface directed toward the exterior surface of the inner tubular member.

A first pressure chamber is defined between the exterior surface of the inner tubular member and the interior surface of the outer tubular member, and between a first distal seal assembly and a first proximal seal assembly. The first pressure chamber is in fluid communication with the first distal flow port. A second pressure chamber is defined between the exterior surface of the inner tubular member and the interior surface of the outer tubular member, and between a second distal seal assembly and a second proximal seal assembly. The second pressure chamber is disposed proximal to the first pressure chamber and in fluid communication with the second distal flow port. The fluid introduced through the fluid lumen pressurizes the first pressure chamber and the second pressure chamber to generate a respective force at the first proximal seal assembly and to the second proximal seal assembly to urge the outer tubular member in the proximal direction.

According to a further aspect of the disclosed subject matter, method of delivering a device is provided, comprising providing a catheter including an inner tubular member having a length, an exterior surface and a fluid lumen defined therein. The exterior surface defines a first distal flow port in fluid communication with the fluid lumen and a second distal flow port located proximal to the first distal flow port in fluid communication with the fluid lumen. The catheter further includes an outer tubular member movable relative to the inner tubular member in a proximal direction along a length of the inner tubular member. The outer tubular member has an interior surface directed toward the exterior surface of the inner tubular member.

A first pressure chamber is defined between the exterior surface of the inner tubular member and the interior surface of the outer tubular member, and between a first distal seal assembly and a first proximal seal assembly. The first pressure chamber is in fluid communication with the first distal flow port. A second pressure chamber is defined between the exterior surface of the inner tubular member and the interior surface of the outer tubular member, and between a second distal seal assembly and a second proximal seal assembly.

The second pressure chamber is disposed proximal to the first pressure chamber and in fluid communication with the second distal flow port. The fluid introduced through the fluid lumen pressurizes the first pressure chamber and the second pressure chamber to generate a respective force at the first proximal seal assembly and to the second proximal seal assembly to urge the outer tubular member in the proximal direction.

The method further includes disposing a device between the exterior surface of the inner tubular member and the interior surface of the outer tubular member at a location distal to the first distal seal assembly. The method also includes introducing fluid into the fluid lumen to pressurize the first pressure chamber and the second pressure chamber to generate a respective force at the first proximal seal assembly and the second proximal seal assembly to move the outer tubular member in the proximal direction to expose the device.

It is to be understood that both the foregoing general description and the following detailed description and drawings are examples and are provided for purpose of illustration and not intended to limit the scope of the disclosed subject matter in any manner.

The accompanying drawings, which are incorporated in and constitute part of this specification, are included to illustrate and provide a further understanding of the devices of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which:

FIGS. 4A-4D are schematic side cross-sections depicting a representative embodiment of a catheter of the disclosed subject matter having a first pressure chamber and a second pressure chamber with an initial expansion space therebetween.

DETAILED DESCRIPTION

Figure 1:
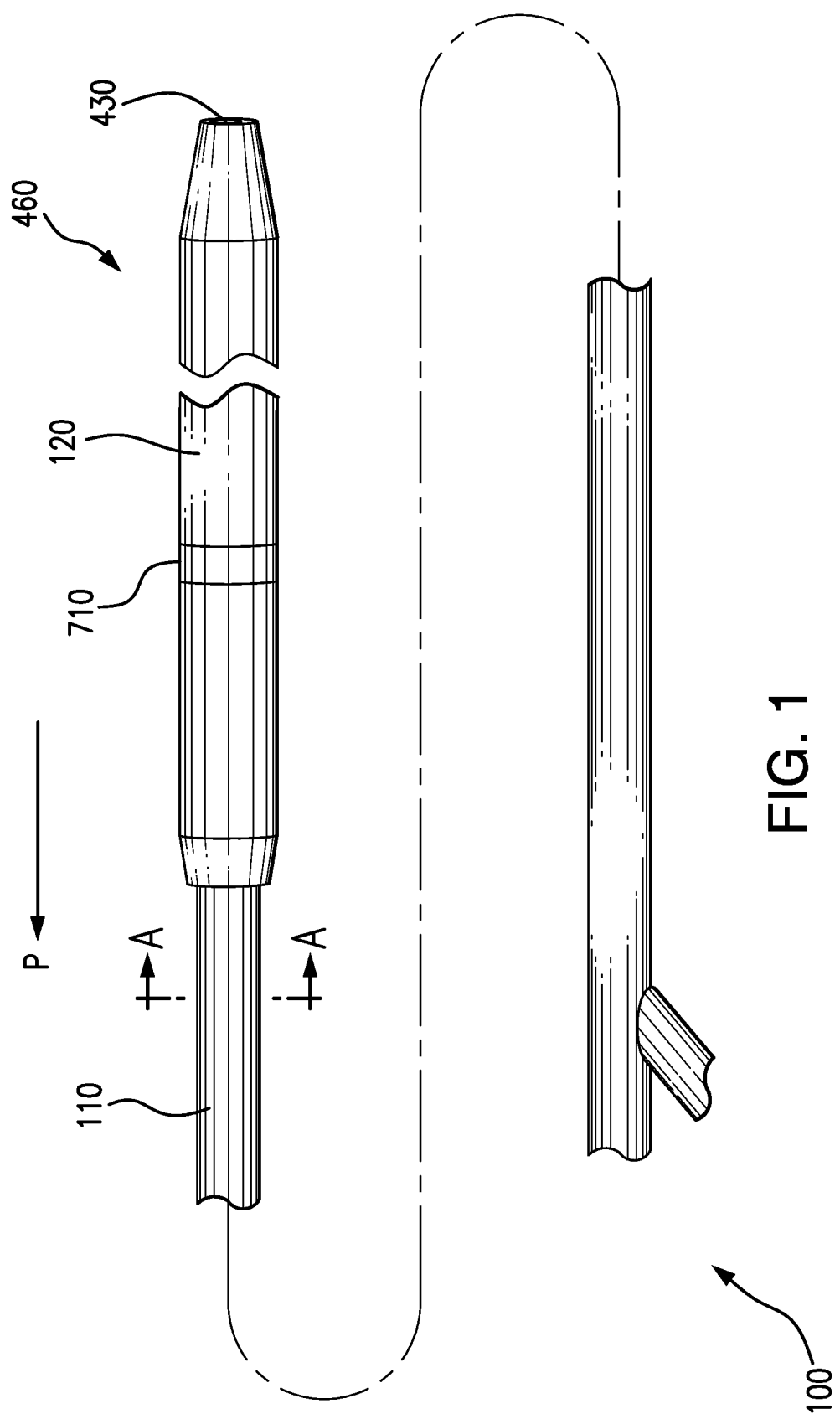
FIG. 1 is a schematic side view of a representative catheter in accordance with the disclosed subject matter.

Reference will now be made in detail to embodiments of the disclosed subject matter, an example of which is illustrated in the accompanying drawings. The disclosed subject matter will be described in conjunction with the detailed description of the system.

In accordance with the disclosed subject matter, a catheter comprising an inner tubular member having a length, an exterior surface and a fluid lumen defined therein is provided. The exterior surface defines a first distal flow port in fluid communication with the fluid lumen and a second distal flow port located proximal to the first distal flow port in fluid communication with the fluid lumen. The catheter further includes an outer tubular member movable relative to the inner tubular member in a proximal direction along a length of the inner tubular member. The outer tubular member has an interior surface directed toward the exterior surface of the inner tubular member.

A first pressure chamber is defined between the exterior surface of the inner tubular member and the interior surface of the outer tubular member, and between a first distal seal assembly and a first proximal seal assembly. The first pressure chamber is in fluid communication with the first distal flow port. A second pressure chamber is defined between the exterior surface of the inner tubular member and the interior surface of the outer tubular member, and between a second distal seal assembly and a second proximal seal assembly. The second pressure chamber is disposed proximal to the first pressure chamber and in fluid communication with the second distal flow port. The fluid introduced through the fluid lumen pressurizes the first pressure chamber and the second pressure chamber to generate a respective force at the first proximal seal assembly and to the second proximal seal assembly to urge the outer tubular member in the proximal direction.

According to a further aspect of the disclosed subject matter, a method of delivering a device is provided, comprising providing a catheter including an inner tubular member having a length, an exterior surface and a fluid lumen defined therein. The exterior surface defines a first distal flow port in fluid communication with the fluid lumen and a second distal flow port located proximal to the first distal flow port in fluid communication with the fluid lumen. The catheter further includes an outer tubular member movable relative to the inner tubular member in a proximal direction along a length of the inner tubular member. The outer tubular member has an interior surface directed toward the exterior surface of the inner tubular member.

A first pressure chamber is defined between the exterior surface of the inner tubular member and the interior surface of the outer tubular member, and between a first distal seal assembly and a first proximal seal assembly. The first pressure chamber is in fluid communication with the first distal flow port. A second pressure chamber is defined between the exterior surface of the inner tubular member and the interior surface of the outer tubular member, and between a second distal seal assembly and a second proximal seal assembly. The second pressure chamber is disposed proximal to the first pressure chamber and in fluid communication with the second distal flow port. The fluid introduced through the fluid lumen pressurizes the first pressure chamber and the second pressure chamber to generate a respective force at the first proximal seal assembly and to the second proximal seal assembly to urge the outer tubular member in the proximal direction.

The method further includes disposing a device between the exterior surface of the inner tubular member and the interior surface of the outer tubular member at a location distal to the first distal seal assembly. The method also includes introducing fluid into the fluid lumen to pressurize the first pressure chamber and the second pressure chamber to generate a respective force at the first proximal seal assembly and the second proximal seal assembly to move the outer tubular member in the proximal direction to expose the device.

The catheter and methods disclosed herein can be used for a variety of treatments of the luminal system of a patient. For example, the disclosed subject matter is particularly suited for treatment of the cardiovascular system of a patient, such as delivery of a medical device into the vasculature.

Solely for purpose of illustration, reference will now be made in detail to specific embodiments, examples of which are illustrated in the accompanying drawings. The examples are not intended to limit the scope of the disclosed subject matter in any manner. For the purposes of this disclosure, like reference numbers in the figures shall refer to like features unless otherwise indicated. Although particular reference is made to various embodiments of a catheter and method for delivering a stent, the catheter and method likewise can be modified for use and delivery of other devices and in other intraluminal systems.

Figure 1A:
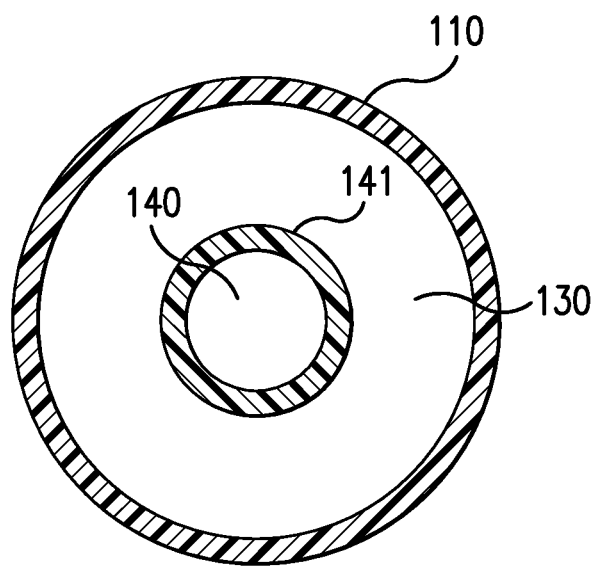
FIG. 1A is a cross-sectional view of an embodiment of the inner tubular member depicting a co-axial configuration taken along the lines A-A of FIG. 1, according to embodiments of the disclosed subject matter.
Figure 1B:
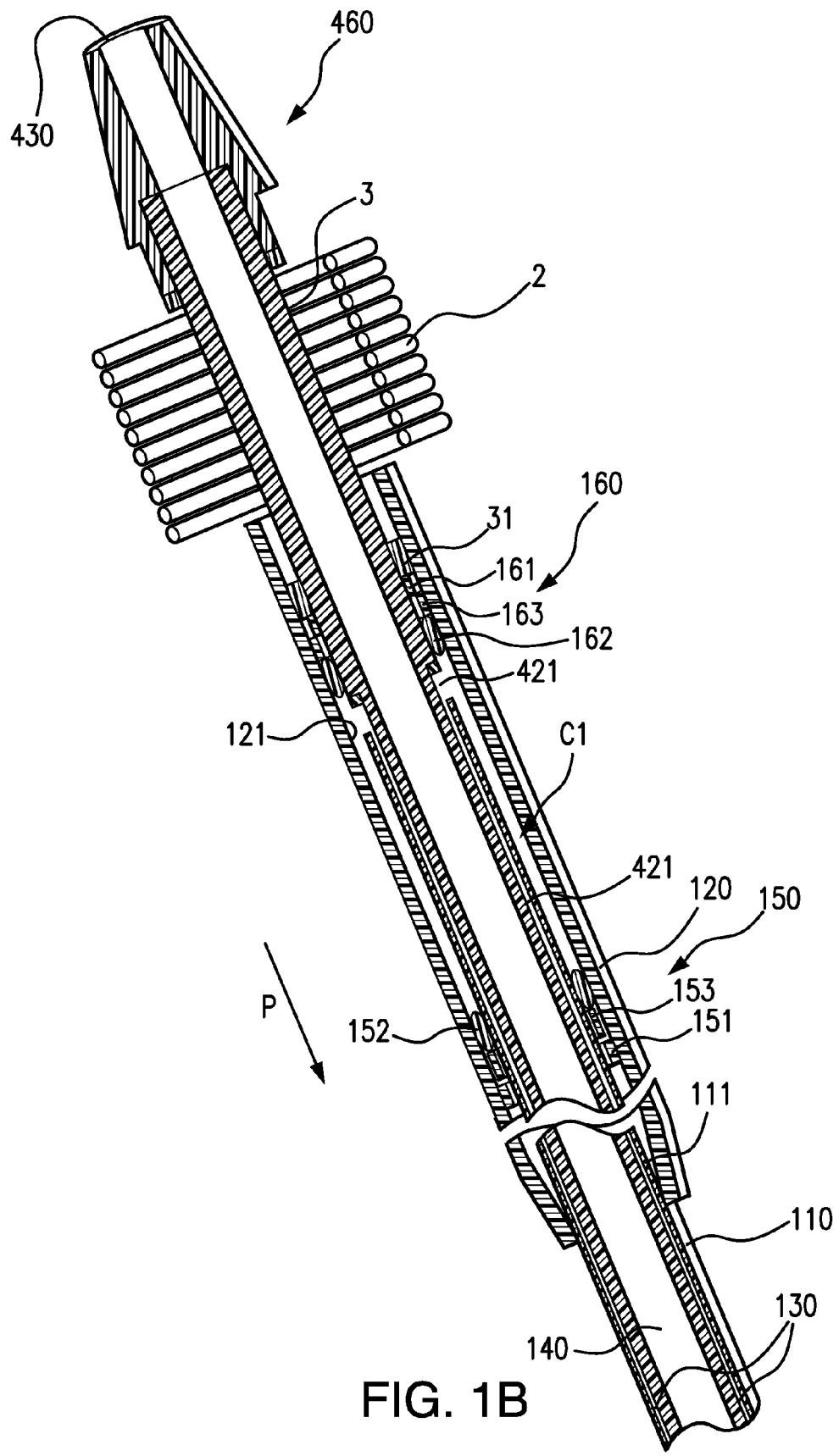
FIG. 1B is an enlarged detail cross-sectional side view of the first pressure chamber of the catheter of FIG. 1, where the guidewire lumen is provided with an over-the-wire configuration.
Figure 1C:
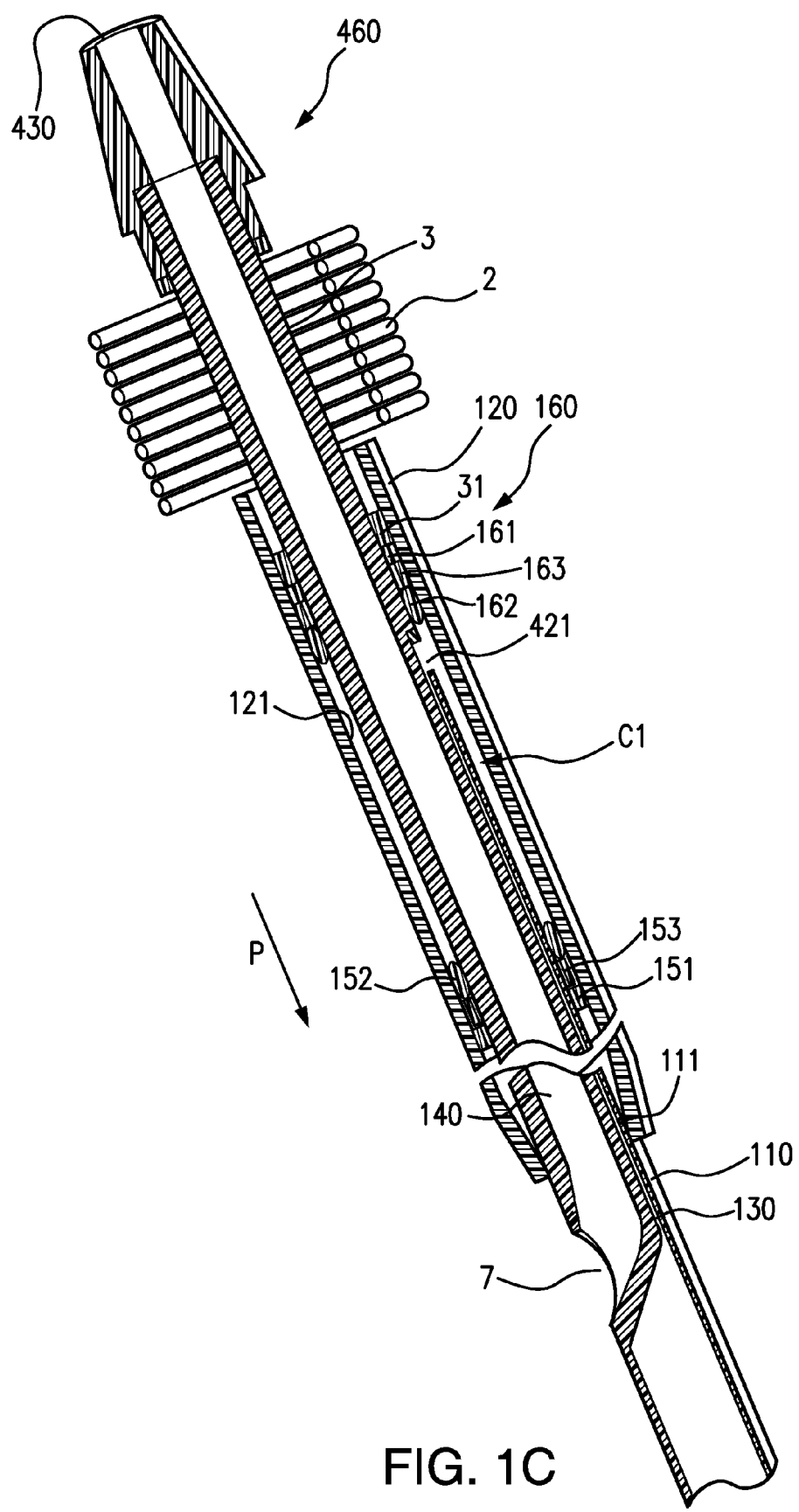
FIG. 1C is an enlarged detail cross-sectional side view of the first pressure chamber of the catheter of FIG. 1, where the guidewire lumen is provided with a rapid exchange configuration.

Solely for purpose of illustration, an embodiment of a hydraulic delivery system, at least a portion of which is delivered within a vasculature or other body lumen, is shown schematically in the accompanying figures. FIGS. 1, 1B and 1C illustrate sections of an example catheter 100. The catheter 100 generally comprises an inner tubular member 110 having a length and an exterior surface wherein the inner tubular member defines at least a fluid lumen therein, as further discussed below. A guidewire receiving lumen can also be provided along at least a portion of the length of the shaft. A guidewire is insertable in the guidewire lumen.

The inner tubular member 110 can include a variety of suitable configurations. Solely for purpose of illustration, FIG. 1B illustrates an over-the-wire (OTW) configuration. In this embodiment, the inner tubular member includes a guidewire lumen 140 that extends generally along the entire length of the inner tubular member In this embodiment, only a first pressure chamber C1 is depicted in FIG. 1B for purposes of clarity. The structure and operation of the pressure chamber C1 will be explained in greater detail below. In accordance with the disclosed subject matter, additional pressure chambers can be provided as described further.

FIG. 1C illustrates a rapid exchange configuration (RX) with only a first pressure chamber C1 depicted for clarity. In this embodiment, a guidewire lumen 140 extends from a proximal guidewire port 147 to a distal end of the inner tubular member 110.

In either the OTW or the RX configuration, the inner tubular member can furthermore have a co-axial arrangement or a multi-lumen arrangement. For example, FIG. 1A depicts a representative cross-sectional view of a co-axial arrangement along lines A-A of FIG. 1. The co-axial arrangement includes inner tubular member 110 with a guidewire tube 141 disposed therein. In this embodiment, the fluid lumen 130 is defined between the inner tubular member 110 and the guidewire tube 141. The guidewire tube 141 furthermore defines the guidewire lumen 140, discussed further below. In this embodiment, the inner tubular member can be a single tube or an assembly of components coupled together.

For purposes of discussion and reference, a co-axial inner tubular member 110 is also shown schematically in FIGS. 1B and 1C. The inner tubular member 110 has a proximal end portion, a distal end portion, and a length. As depicted in FIGS. 1B and 1C, the inner tubular member 110 includes a guidewire lumen 140 defined at least along a length of the inner tubular member 110, as well as a fluid lumen 130 therein.

The guidewire lumen 140 therefore can be defined at least in part by a separate guidewire tube 141 disposed within the fluid lumen 130 of the inner tubular member 110 and sealed at either end, as further discussed herein. The guidewire lumen 140 can house a guidewire therein. In the OTW catheters such as the catheter of FIG. 1B, the guidewire lumen 140 extends along the length of the catheter 100. In contrast, in RX catheters such as the catheter of FIG. 1C, the guidewire lumen 140 extends along a portion of the length of the catheter along a distal end. The guidewire lumen 140 includes a proximal guidewire port 147 at a proximal end of the guidewire lumen; e.g., depending on whether the catheter is an OTW catheter or an RX catheter. The guidewire lumen has a distal guidewire port 430 at a distal end of the catheter 100. For example, and as embodied herein, the catheter 100 has a distal tip 460 at the distal end to define a distal guidewire port 430, as shown in FIG. 1. The distal tip 460 can further define the distal end for a stent seat 3 or the like, as described further below and depicted in FIG. 1B.

Figure 2A:
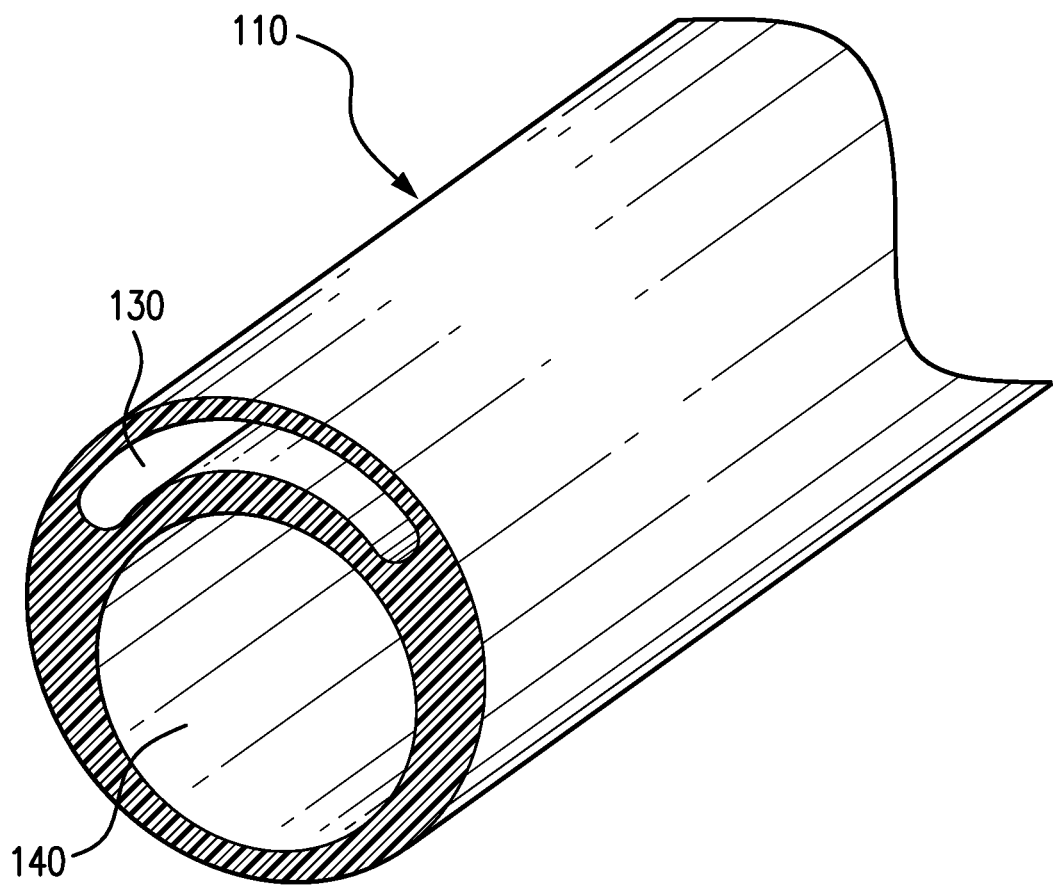
FIG. 2A is a cross-sectional perspective view an embodiment of the inner tubular member depicting a monolithic multi-lumen configuration taken along the lines A-A of FIG. 1, according to embodiments of the disclosed subject matter.

Alternatively, and solely for purpose of illustration, FIG. 2A depicts a representative cross-sectional view of a multi-lumen arrangement. For example, but not limited thereto, the inner tubular member 110 can be a monolithic member with a multi-lumen configuration. In such embodiment, the inner tubular member 110 defines both a guidewire lumen 140 and a fluid lumen 130 therein.

In either embodiment, the fluid lumen 130 defines a pathway for fluid to be introduced to the distal end of the inner tubular member from a proximal end of the catheter 100. An adapter can be provided at the proximal end of the catheter for access to the fluid lumen and can be configured to be connected to a fluid source (not shown). Therefore, the fluid can be in communication between the adaptor and the distal flow ports at the distal end of the inner tubular member via the fluid lumen 130, as further discussed herein.

A conventional device, such as but not limited to an indeflator or a syringe, can introduce the fluid to the fluid lumen. The indeflator can be provided to control the inflation and deflation of the pressure chambers and expansion spaces. The indeflator can further include a thread engagement or locking mechanism to control pressurization and depressurization of the pressure chamber (not shown). Additionally, a pressure gauge can be provided with the indeflator to monitor the pressure system of the catheter. The indeflator can also be configured to allow for the rapid release of hydraulic pressure to stop or inhibit the deployment of the stent. The indeflator can also be configured to create and/or maintain negative pressure in the catheter. The indeflator can have a locking mechanism to maintain negative pressure in the catheter. The indeflator can further create a vacuum that decreases the profile of the catheter. For example, by creating a vacuum, the outer tubular member disclosed herein can be configured to decrease in profile and/or lock in position. An example of a suitable indeflator is an Atrion indeflator Atrion Medical—55ATM.

In an alternate embodiment, the fluid lumen and the guidewire lumen are formed as a single shared lumen. For such co-axial arrangements, fluid can thus flow within the shared lumen and the guidewire is insertable into the shared lumen. In such a configuration, the inner tubular member can comprise proximal and distal guidewire seals disposed in the shared lumen to sealingly engage the guidewire disposed within the fluid lumen. Alternatively, the guidewire lumen can be formed by a thin membrane of suitable strength to prevent the guidewire from penetrating there through and disposed within and along the length of the fluid lumen in a coaxial configuration. Schematic depiction of a shared lumen configuration (with the seals not shown for clarity) and/or of the co-axial member configuration (with the thin membrane omitted for clarity) are provided in FIGS. 4A-D, as further discussed herein. Although omitted for clarity in FIGS. 4A-D for purpose of demonstrating the flow of fluid within the chambers, it is recognized that stop 31 includes a guidewire lumen extending therethrough. Such shared or membrane coaxial configurations allow for reduced diameter of the inner tubular member, and thus reduced profile of the catheter.

Figure 5:
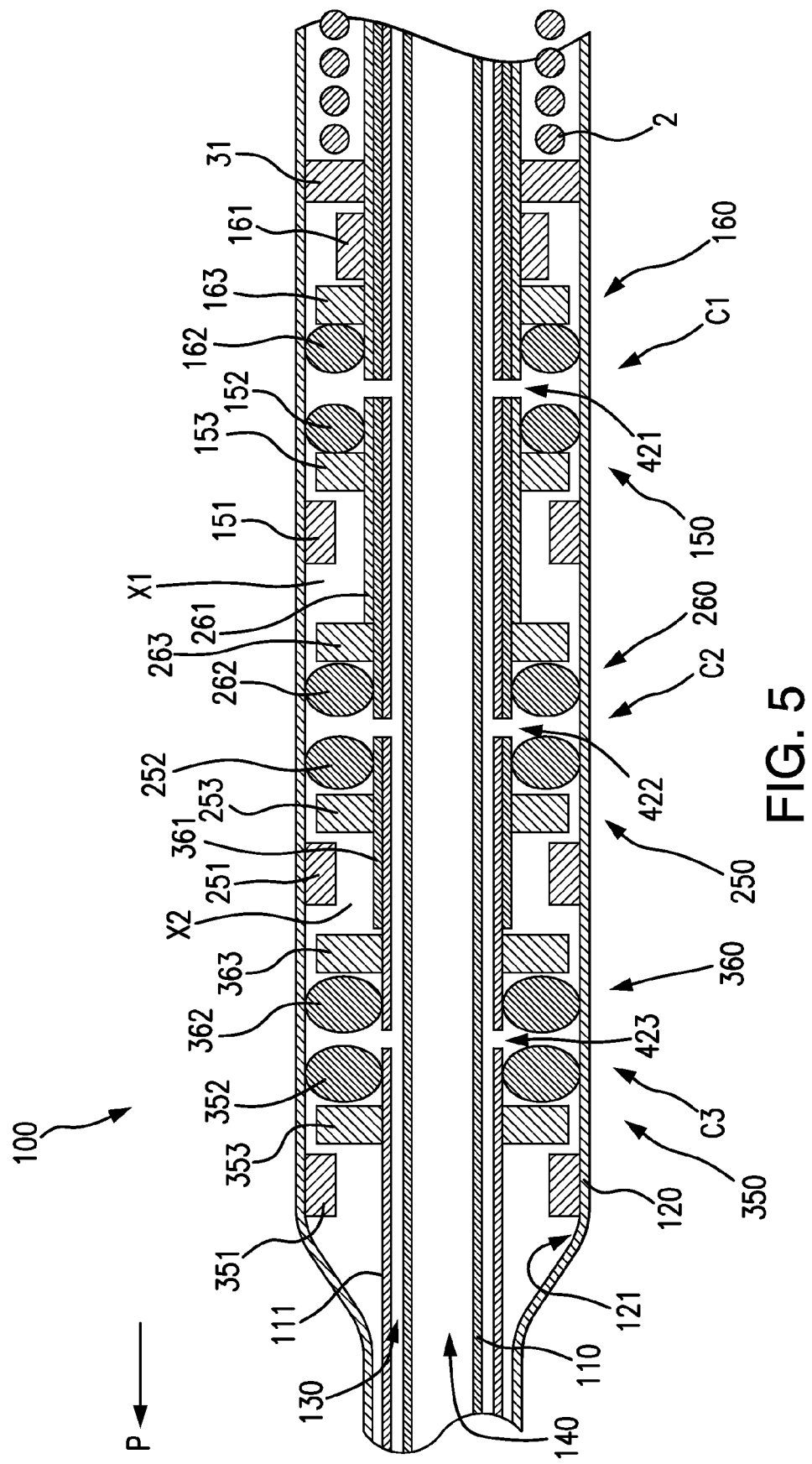
FIG. 5 is a schematic side cross-section of a distal end of a catheter of the disclosed subject matter having three pressure chambers with initial expansion spaces therebetween.

With reference to FIG. 1B, the exterior surface 111 defines a first distal flow port 421 along the distal end portion of inner tubular member 110, which is in fluid communication with the fluid lumen 130. Fluid can travel through the fluid lumen 130 and exit the fluid lumen 130 at the first distal flow port 421. As further disclosed herein, the exterior surface 111 can define a plurality of flow ports. As depicted in FIG. 4A and FIG. 5, a second distal flow port 422 is defined by the exterior surface 111 along the distal end portion of the inner tubular member 110, where the second distal flow port 422 is also in fluid communication with the fluid lumen 130. The second distal flow port 422 is disposed proximal to the first distal flow port 421. As provided in FIG. 5, a third or additional distal flow port 423 can also be provided disposed proximal to the second distal flow port 422, as necessary or desired.

Each flow port defines an access point for fluid communication between the fluid lumen 130 and an environment surrounding the exterior surface 111. If desired, each flow port can be provided with two or more exit locations to the surrounding environment, as depicted in FIG. 1B. Alternatively, each flow port can be provided with only one exit location to the surrounding environment as depicted in FIG. 1C. In accordance with an alternate embodiment, a separate fluid lumen can be provided for each distal flow port respectively.

Figure 3:
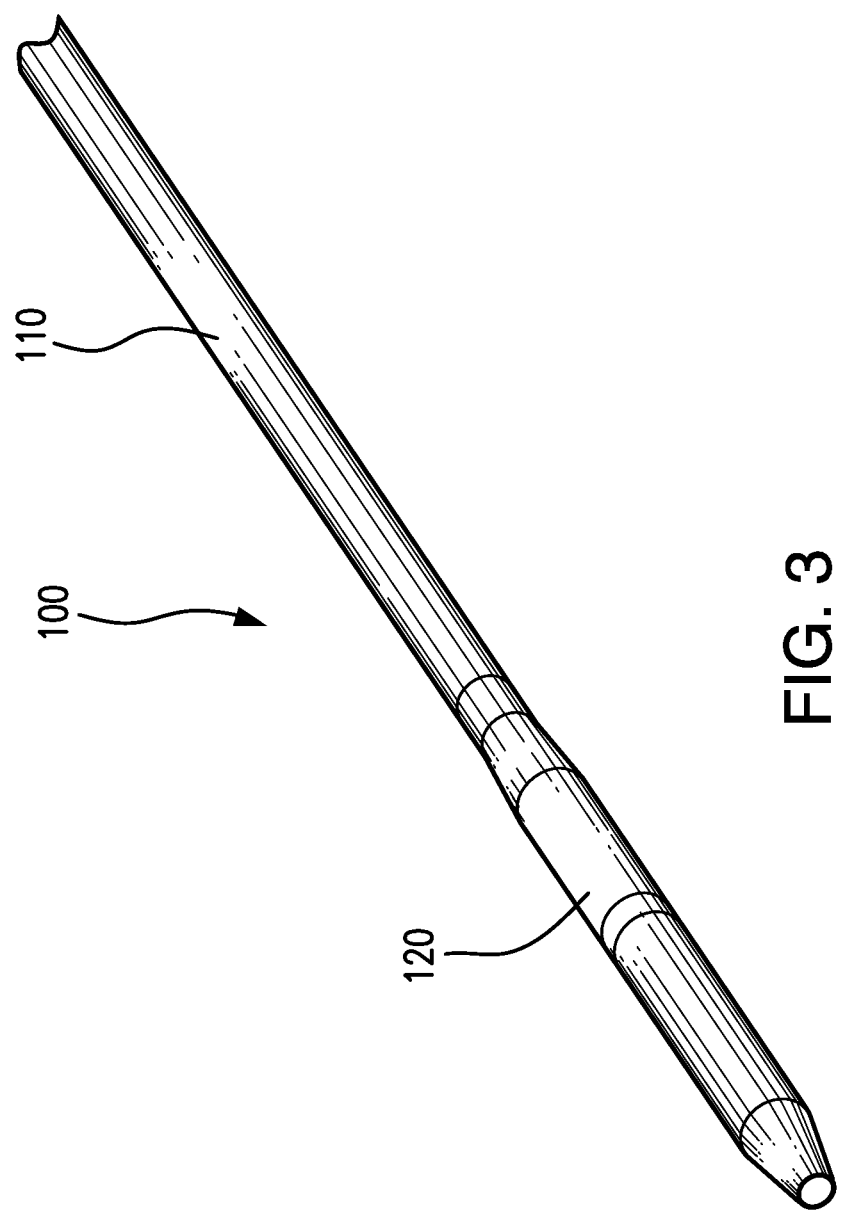
FIG. 3 is a perspective view of a distal end section of the catheter of FIG. 1.

As depicted in FIGS. 1, 1B, and 1C, the catheter 100 further includes an outer tubular member or sheath 120. The outer tubular member 120 has a proximal end, a distal end, a length, and an interior surface 121, as shown in FIGS. 1B and 1C. The inner tubular member 110 is positioned within the outer tubular member 120 at least at the distal end of the catheter 100. As such, the exterior surface 111 of the inner tubular member 110 is directed toward the interior surface 121 of the outer tubular member 120 such that the inner tubular member 110 is positioned within the outer tubular member 120. The outer tubular member 120 is movable relative to the inner tubular member 110 along a length of the inner tubular member 110. The outer tubular member 120 can be retracted in a direction P toward the proximal end of the catheter. As shown in FIGS. 1 and 3, the outer tubular member 120 can be disposed only at a distal end portion of the catheter to reduce profile and increase flexibility of a proximal section of the catheter, if desired. As described further herein, the catheter of the disclosed subject matter can be configured to deliver a medical device, such as the stent 2, of any suitable length. That is, the catheter can be configured to generate a force sufficient to retract the outer tubular member, wherein the generated force is greater than the resistance force caused by the medical device acting on the outer tubular member.

Further in accordance with the disclosed subject matter and as shown in FIG. 5, the catheter includes a first pressure chamber C1 defined between the exterior surface 111 of the inner tubular member 110 and the interior surface 121 of the outer tubular member 120, and between a first distal seal assembly 160 and a first proximal seal assembly 150, as further described below. Additionally, and as described further, one or more additional chambers are provided proximal to the first pressure chamber. FIG. 4A depicts a schematic cross-sectional view of a representative embodiment of a catheter having the first pressure chamber C1. The catheter 100 includes the first pressure chamber C1 in fluid communication with the first distal flow port 421. The first pressure chamber C1 assists in retracting the outer sheath 120 in a proximal direction P. As best seen in FIG. 5, the first pressure chamber C1 is a substantially sealed chamber defined between the exterior surface 111 of the inner tubular member 110 and the interior surface 121 of the outer tubular member 120. Furthermore, a first proximal seal assembly 150 and a first distal seal assembly 160 define the proximal and distal ends of the first pressure chamber C1, respectively. The first pressure chamber C1 receives fluid from the fluid lumen 130 via the first distal flow port 421. The pressure chamber C1 has an initial volume.

As depicted in FIG. 5, the first distal seal assembly 160 is distal to the first distal flow port 421 and includes a first distal seal 162 and a first distal stop 161. The first distal seal 162 is disposed proximal to the first distal stop 161. The first distal stop 161 extends from the exterior surface 111 of the inner tubular member toward the interior surface 121 of the outer tubular member. The first distal stop 161 inhibits movement of the first distal seal 162 in a distal direction (which is opposite to proximal direction P). The first distal seal assembly 160 can also include a first distal bushing 163 as shown in the embodiment of FIG. 5, solely for purpose of illustration. The first distal bushing 163 provides a backing or similar structure to the first distal seal 162 and is disposed between the first distal stop 161 and the first distal seal 162. The first distal bushing 163 is not attached to the outer tubular member 120 so as to allow the outer tubular member 120 to retract or otherwise slide freely across the first distal bushing 163. Alternatively, the first distal seal assembly 160 can be a single or monolithic element extending from the exterior surface 111 of the inner tubular member 110 and sealingly engaging the interior surface 121 of the outer tubular member. In other embodiments, the first distal seal assembly 160 can comprise multiple elements extending from the exterior surface 111 of the inner tubular member.

The first pressure chamber C1 also includes a first proximal seal assembly 150. As further embodied herein, the first proximal seal assembly 150 is disposed proximal to the first distal flow port 421 and includes a first proximal seal 152 and a first proximal stop 151. The first proximal seal 152 is disposed distal to the first proximal stop 151. The first proximal stop 151 extends from the interior surface 121 of the outer tubular member. The first proximal seal assembly 150 can further include a first proximal bushing 153 as shown solely for purpose of illustration, as shown in the embodiment of FIG. 5. The first proximal bushing 153 provides a backing to the first proximal seal 152 and is disposed between the first proximal stop 151 and proximal to the first proximal seal 152. Alternatively, the first proximal seal assembly 150 can be a single or monolithic element extending from the interior surface 121 of the outer tubular member 120 and sealingly engaging the exterior surface 111 of the inner tubular member 110. In other embodiments, the first proximal seal assembly 150 can comprise multiple elements. As embodied herein one or both of the proximal and distal seal can form a wiper seal across the corresponding surface as known.

As best seen in FIG. 4A, the catheter 100 further includes a second pressure chamber C2 proximal to the first pressure chamber C1. The second pressure chamber C2 generally operates in tandem with the first pressure chamber C1 and operates in a similar manner to the first pressure chamber C1. The first pressure chamber C1 and the second pressure chamber C2 can collectively generate an initial resulting retraction force to urge the outer tubular member 120 initially in the proximal direction P. FIG. 4A depicts a schematic cross-sectional view of the second pressure chambers at a distal end section of the catheter 100 of FIG. 1.

The second pressure chamber C2 is in fluid communication with the second distal flow port 422. As best seen in FIG. 5, the pressure chamber C2 is a substantially sealed chamber defined between the exterior surface 111 of the inner tubular member 110 and the interior surface 121 of the outer tubular member 120. A second proximal seal assembly 250 and a second distal seal assembly 260 are provided to define the proximal and distal ends of the second pressure chamber. The second pressure chamber C2 receives fluid from the fluid lumen 130 via the second distal flow port 422. The second pressure chamber C2 has an initial volume.

The second distal seal assembly 260 is distal to the second distal flow port 422 and includes a second distal seal 262 and a second distal stop 261. The second distal seal 262 is disposed proximal to the second distal stop 261. The second distal stop 261 extends from the exterior surface 111 of the inner tubular member toward the interior surface 121 of the outer tubular member. The second distal seal assembly 260 is free to move in the proximal direction P, but inhibited from movement in the distal direction (which is opposite the proximal direction P) by the second distal stop 261. Additionally, and as embodied herein, the second distal stop 261 can comprise a platform, a step, a raiser, conical bump, a wedge shape, a one-way deflector, or the like coupled to or formed on the exterior surface 111 of the inner tubular member.

For example, and with reference to the embodiments of FIG. 4A and FIG. 5, the second distal stop 261 can be formed by a sleeve or similar member on the exterior surface 111 of the inner tubular member. In this manner, the sleeve forms a portion of the exterior surface upon which the first proximal seal 152 can travel during retraction of the outer tubular member. The proximal end of the sleeve defines the second distal stop, in the form of a stop, to inhibit movement of the second distal seal 262 in the distal direction, but allow movement of the second distal seal in the proximal direction P. Likewise the first proximal seal 150 can travel or move proximally across the step defined by the proximal end of the sleeve without inhibition. The first proximal seal 150 can be configured to maintain a seal between the exterior surface 111 of the inner tubular member 110 and the interior surface 121 of the outer tubular member 120 even after moving proximal to the proximal end of the sleeve, or the first proximal seal 150 can be configured to allow leakage thereacross when proximal to the proximal end of the sleeve.

Figure 6A:
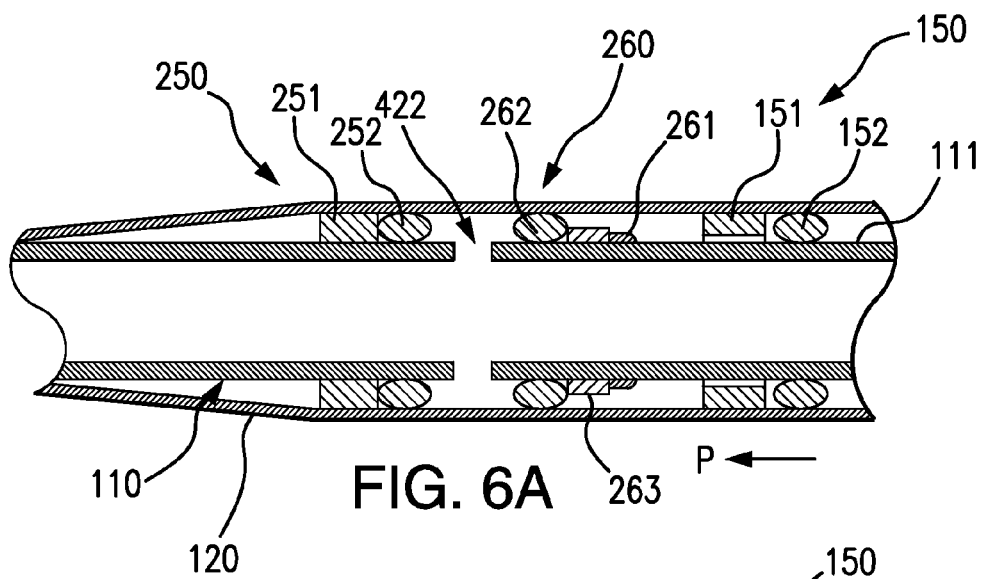
FIGS. 6A-C are schematic side cross-sections of an embodiment of a one-way distal stop configuration between adjacent pressure chambers during deployment.
Figure 6B:
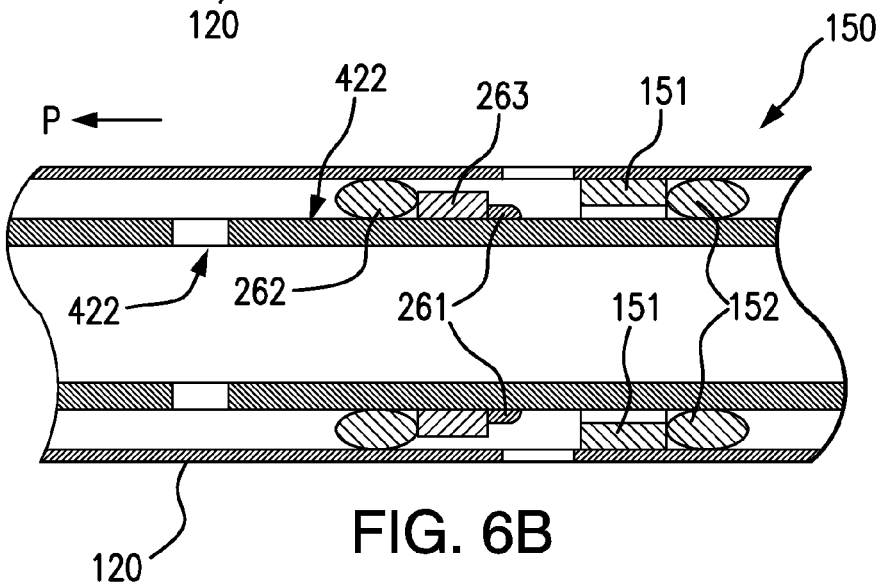
Figure 6C:
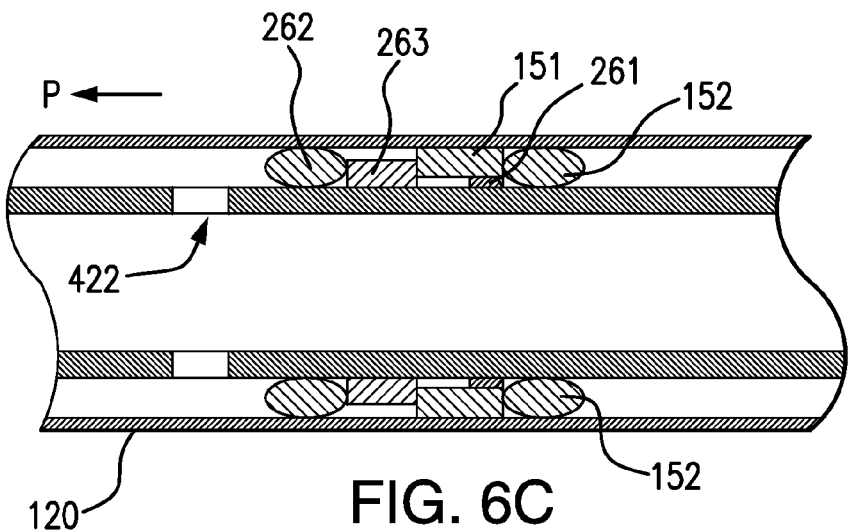

FIGS. 6A-6C illustrate an alternative embodiment in which a one-way stop is defined, wherein the second distal stop 261 comprises a bump having, for example, but not limited to a conical or wedge shape. In this embodiment, the bump 261 is coupled to or formed on the exterior surface 111 of the inner tubular member and disposed distal to the second distal seal assembly 260. The bump 261 provides a one-way stop to prevent the second distal seal assembly 260 from moving in the distal direction (which is opposite the proximal direction P) while further allowing first proximal seal assembly 150 to move in the proximal direction P. The narrowest end of the bump 261 is directed distally to create a ramp-like structure for the first proximal seal assembly 150 to travel up and over the bump in a proximal direction. The bump is dimensioned so that the proximal seal assembly 150 of the distal chamber can slide proximally across the bump while preventing the second distal seal assembly 260 of the proximal chamber from moving distally. In this manner, the first proximal seal assembly 150 can maintain a seal between the exterior surface of the inner tubular member and the interior surface of the outer tubular member 120 even after traveling across and moving proximally to the bump 261.

As best seen in FIG. 5, the second distal seal assembly 260 can also include a second distal bushing 263. The second distal bushing 263 provides a backing to the second distal seal 262 and is disposed between the second distal stop 261 and the second distal seal 262. The second distal bushing 263 is free to slide with the outer tubular member. Alternatively, the second distal seal assembly 260 can be a single or monolithic element extending from the exterior surface 111 of the inner tubular member 110 and sealingly engaging the interior surface 121 of the outer tubular member. In other embodiments, the second distal seal assembly 260 can comprise multiple elements extending from the exterior surface 111 of the inner tubular member.

The second proximal seal assembly 250 is disposed proximal to the second distal flow port 422 and includes a second proximal seal 252 and a second proximal stop 251. The second proximal seal 252 is disposed distal to the second proximal stop 251. The second proximal stop 251 extends from the interior surface 121 of the outer tubular member 120 toward the exterior surface 111. The second proximal seal assembly 250 can further include a second proximal bushing 253 as shown for purposes of illustration and is not limited thereto, as depicted in the embodiments of FIG. 5. The second proximal bushing 253 provides a backing to the second proximal seal 252 and is disposed proximal to the second proximal seal 252.

In accordance with another aspect of the disclosed subject matter, a first expansion space X1 is defined between the exterior surface 111 of the inner tubular member and the interior surface 121 of the outer tubular member, and located between the first pressure chamber C1 and the second pressure chamber C2. The first expansion space X1 can initially be vacuum sealed and/or can be filled with a compressible fluid, such as $CO_2$, an inert gas, a biocompatible gas, or the like. The first expansion space X1 allows for expansion of the first pressure chamber C1 towards the second pressure chamber C2.

For example, and with reference to the embodiment of FIGS. 4A-C, pressurized fluid introduced into the fluid lumen 130 will enter the first pressure chamber C1 via the first distal flow port 421 and enter the second distal flow port 422. For purpose of clarity, the guidewire and guidewire lumen are not depicted. As shown in FIG. 4B, the first and second distal seal assemblies remain stationary relative to the inner tubular member 110. However, the first proximal seal assembly 150 will be urged proximally by the pressure within the first pressure chamber C1 and thus travel toward the second distal seal assembly 260. As the first proximal seal assembly 150 travels proximally, the first pressure chamber C1 will increase in volume, and the first expansion space X1 will decrease in volume. This travel will continue until the first proximal seal assembly 150 contacts the second distal seal assembly 260, or at least a portion thereof as shown in FIG. 4B. With continued pressurization of the first pressure chamber C1, the first proximal seal assembly 150 will urge the second distal seal 262 and second distal bushing 263, if provided, in a proximal direction P until disposed proximal of the second distal flow port 422 as shown on FIG. 4C.

The catheter 100 can optionally further include additional pressure chambers as well as expansion spaces disposed at least initially between adjacent pressure chambers. For example, FIG. 5 shows a third pressure chamber C3 provided proximal to the second pressure chamber C2. The third pressure chamber C3 works in tandem with the first pressure chamber C1 and the second pressure chamber C2 and generally operates in a similar manner to the pressure chambers, as discussed herein.

Solely for purpose of illustration, FIG. 5 depicts the third pressure chamber C3 in fluid communication with a third distal flow port 423. The third pressure chamber C3 receives fluid from the fluid lumen 130 via the third distal flow port 423. The pressure chamber C3 is a substantially sealed chamber defined by the exterior surface 111 of the inner tubular member 110 and the interior surface 121 of the outer tubular member 120. A third proximal seal assembly 350 and a third distal seal assembly 360 are provided to define the proximal and distal ends of the third pressure chamber C3. The pressure chamber C3 has an initial volume.

The third distal seal assembly 360 is distal to the third distal flow port 423 and includes a third distal seal 362 and a third distal stop 361. The third distal seal 362 is disposed proximal to the third distal stop 361. The third distal stop 361 extends from the exterior surface 111 of the inner tubular member toward the interior surface 121 of the outer tubular member. The third distal seal 362 is disposed proximal to the third distal stop 361. The third distal seal assembly 360 is free to move in the proximal direction P, but inhibited from movement in the distal direction (opposite the proximal direction) by the third distal stop 361. Additionally, and as embodied herein, the third distal stop 361 can comprise a platform, step, raiser, sleeve, conical bump, wedge shape, a one-way deflector or the like coupled to or formed on the exterior surface 111 of the inner tubular member, as previously described above.

For example, and with reference to the embodiment of FIG. 5, the third distal stop 361 can be formed by a sleeve or similar member on the exterior surface of the inner tubular member, as similarly described above.

The third distal seal assembly 360 can also include a third distal bushing 363, as shown for illustration and not limited thereto, in the embodiments of FIG. 5. The third distal bushing 363 provides a backing to the third distal seal 362 and is disposed between the third distal stop 361 and the third distal seal 362. The third distal bushing 363 is free to slide in the proximal direction P. Alternatively, the third distal seal assembly 360 can be a single or monolithic element extending from the exterior surface 111 of the inner tubular member 110 and sealingly engaging the interior surface 121 of the outer tubular member. In other embodiments, the third distal seal assembly 360 can comprise multiple elements extending from the exterior surface 111 of the inner tubular member.

The third proximal seal assembly 350 is disposed proximal to the third distal flow port 423 and includes a third proximal seal 352 and a third proximal stop 351. The third proximal seal 352 is disposed distal to the third proximal stop 351. The third proximal stop 351 extends from the interior surface 121 of the outer tubular member. The third proximal seal assembly 350 can further include a third proximal bushing 353. The third proximal bushing 353 provides a backing to the third proximal seal 352 and is disposed between the third proximal stop 351 and proximal the third proximal seal 352.

With reference to the embodiment of FIG. 5, a second expansion space X2 can be provided between the second pressure chamber C2 and the third pressure chamber C3. The second expansion space X2 is configured and operated in a manner similar to that of the first expansion space X1, as described above with reference to FIG. 4A-4C.

As relatively high fluid pressures are needed to urge the retraction of the outer tubular member 120, the pressure chambers are formed to withstand operating pressures with minimal to no leaks. A variety of suitable seal constructions and materials can be used, such as, but not limited to, sliding seals, rings, cups seals, lips seals, and compressed bushings. In one embodiment, the catheter 100 further includes a bellows, or bladder component within each pressure chamber to prevent leaks. The bellows or bladder component is coupled to the exterior surface of the inner tubular member 110 and is in fluid communication with the flow ports 421, 422, and 423, wherein fluid introduced through the flow ports expands the component to assist in retracting the outer tubular member.

Embodiments of the disclosed subject matter provide for the pressure chambers capable of handling a wide range of suitable pressures. Solely for purpose of illustration, in one embodiment the pressure chamber can handle a positive pressure of up to 750 psi, and a negative pressure of approximately 14 psi.

In accordance with another aspect of the disclosed subject matter, the pressure chambers can be configured to increase in cross section when pressurized, such that a greater force is generated on the end seal due to the increased surface area. The pressure chambers can be constructed to expand as pressurized, yet maintain adequate hoop strength at the distal end section to retain the constrained stent. In this embodiment, outer tubular member can be constructed of a suitable material or composite of materials to allow the outer tubular member to expand as the pressure chamber is pressurized.

The seals 152, 162, 252, 262, 352, 362, and the guidewire seals, if provided, can each be formed as a separate member and attached to the corresponding tube member, or can be formed as part of the tubular member. The seals can be formed of any suitable materials. Solely for purpose of illustration, the seal can be rubber or silicon. In other embodiments, the seal can be formed of a low durometer rubber having a compressed condition and an expanded condition. The seal can be significantly crushed and deformed in the initial delivery configuration, transitioning to the expanded condition when the pressure chamber is pressurized. Alternatively, the seal can be made of hydrophilic polymers that absorb fluid in the pressure chamber and expand along with the outer tubular member.

Solely for purpose of illustration, hydrophilic material, such as, but not limited to, HydroMed™, Hydrothane™, Hydak$^{(R)}$, can be used for the seals. Seals made of such material can be configured to swell when exposed to an aqueous environment, thus sealing more tightly while maintaining lubricity. The seals can comprise an expandable material or composite of materials to increase accordingly to match the dimensions of the outer tubular member. That is, the seal expands with the outer tubular member to maintain an adequate seal. As the pressure chamber expands, the exposed surface area of the seal also increases, resulting in a proportional increase in retraction force at a given fluid pressure. Thus, an expanding pressure chamber provides for greater retraction force at a given pressure. Alternatively, the seals can be made of hydrophobic material to be used with a suitable pressurized fluid. Solely for purpose of example, silicone seals with a Hydromer 2314-172 coating can be used. Additionally or alternatively, a high viscosity hydraulic fluid can be used to further inhibit leaks across the seals. In another embodiment, O-rings can be used for the seal constructions comprised of silicone, buna, or other suitable elastomers. Furthermore, for purpose of example, but not limited thereto, the seal can include soft tubing such as a low durometer Pebax.

Similarly, the bushings can be constructed of any suitable material, including, but not limited to, PEEK, Pebax, polyethylene, HDPE, mixtures of HDPE and LDPE, a blend of Nylon L75/L25, and the like. Additionally, the bushings can comprise a metallic material, a combination low density polyethelene, silicon, nitril, soft Pebax 30, or other blends of suitable material, and can be coated with a suitable material as is known in the art. In accordance with another aspect of the disclosed subject matter, spacer elements or O-rings (not shown) can be provided within the pressure chambers. The spacer elements can prevent the outer tubular member and seals from being collapsed during delivery and storage of the catheter. The spacer elements can also reduce the amount of fluid needed to retract the outer tubular member. The spacer elements can be made of any of a variety of suitable shapes and materials, such as ring members having diameters to fit within the inner and outer diameters of the inner and outer tubular members, respectively. Alternatively, the proximal and distal seals can be coated with a hydrophobic layer such as for example oil or wax, or the seals can be made of hydrophobic material such as a fluorocarbon or olefins like polypropylene or other hydrophobic materials suitable to be used with a pressurized fluid.

In accordance with another aspect of the disclosed subject matter, and as embodied herein in FIGS. 1B and 1C, for purposes of discussion, a seat such as the stent seat 3 can be defined distal to the pressure chambers for delivery of a medical device. For example, the catheter 100 can include an intravascular prosthesis, such as a stent 2, positioned on the stent seat 3 such that the stent 2 is positioned between the inner tubular member 110 and the outer member 120 at the distal end of the catheter 100. The outer member 120 retains the stent 2 in a compressed or delivery condition in a first position. When the outer member 120 is retracted by the pressure chambers working in tandem, the stent 2 is allowed to expand to a second position as shown in FIGS. 4-6, further discussed above and below. The self-expanding stent 2 is exposed by the movement of the outer member or sheath 120 in the proximal direction P.

If desired, a bumper or stop member can be positioned proximal to the stent 2 to act as a stent seat. For example and as provided in FIG. 5, in accordance with another aspect of the disclosed subject matter, the catheter 100 can include a stop 31 secured to the inner tubular member 110. The stop 31 can be formed as the first distal stop 161 as shown in FIGS. 4A-4D or can be disposed distal to the first distal stop 161 and proximal to the medical device to be delivered, e.g. the stent 2. Although the guidewire lumen and guidewire are omitted for clarity in FIGS. 4A-D for purpose of demonstrating the flow of fluid within the chambers, it is recognized that stop 31 includes a guidewire lumen extending therethrough. The stop 31 can be made of or include a radiopaque material. The radiopacity can provide enhanced visibility for the suitable placement of the catheter at the treatment site. The stop 31 can thus be a radiopaque marker. For example, the marker can be a radiopaque metallic ring, or made of a tungsten loaded polymer for increased softness and flexibility. Other suitable markers known can be used.

In accordance with an embodiment of the disclosed subject matter, a method of deploying a catheter as previously described is provided. In the embodiment of FIGS. 4A-4D, pressurized fluid is introduced into the fluid lumen 130 through the adaptor (not shown). As fluid is introduced, the fluid enters the first pressure chamber C1 and the second pressure chamber C2 generally in tandem via the first distal flow port 421 and the second distal flow port 422, respectively. When a suitable volume of fluid has entered the two pressure chambers, the pressure chambers C1 and C2 pressurize and an internal force develops therein. The pressure chambers C1 and C2 cooperate together to urge the outer tubular member in the proximal direction P.

The following description within the pressure chambers C1, C2 provide an example of the collective cooperation of the pressure chambers C1, C2 with expansion space X1 initially defined therebetween to urge the outer tubular member in the proximal direction P. Other suitable operation is further contemplated.

As fluid is introduced into the first pressure chamber C1, the first proximal seal 152 and the first distal seal 162 seal the fluid within the first pressure chamber C1, as depicted in FIG. 4A. Once the amount of fluid that enters the first pressure chamber C1 exceeds the initial volume of the first pressure chamber C1, the first pressure chamber C1 pressurizes and an internal force develops within the chamber C1. Since the stop 31 (acting as the first distal stop 161 in this embodiment) is fixed to the exterior surface 111 and is not movable relative the inner tubular member, the internal force urges the first proximal seal 152 in the proximal direction P against the first proximal stop 151 relative the inner tubular member. In turn, the relatively movable first proximal stop 151, and hence the outer tubular member 120, are urged in the proximal direction P.

Simultaneously the fluid enters each pressure chamber in tandem, as depicted in FIGS. 4A and 4B. As such, the above operation within first pressure chamber C1 similarly occurs in the second pressure chamber C2. For instance, fluid enters the second pressure chamber C2 in tandem as fluid enters the first pressure chamber C1. As fluid enters the second pressure chamber C2, the second proximal seal 252 and the second distal seal 262 seal fluid within the second pressure chamber C2. Once the amount of fluid that enters the second pressure chamber C2 exceeds the initial volume of the second pressure chamber C2, the second pressure chamber C2 pressurizes and an internal force develops within the chamber C2. Since the second pressure chamber C2 and the first pressure chamber C1 both receive fluid from the same fluid lumen 130, and both chambers are of substantially similar size as embodied herein for illustration, the chambers C1 and C2 will reach their maximum initial volume at approximately the same time. If one of the pressure chambers reaches its maximum initial volume prior to the other pressure chamber(s), then the fluid entering the fluid lumen generally balances the pressure within the other chamber.

Similarly, since the second distal stop 261 is fixed to the exterior surface 111 and is not movable, the internal force causes the second proximal seal 252 to engage against the second proximal stop 251. In turn, the movable second proximal stop 251 moves in the proximal direction P in tandem with the movable first proximal stop 151 in the proximal direction P. As the second proximal stop 251 moves in tandem with the first proximal stop 151, the outer tubular member 120, being attached to the second proximal stop 251 and the first proximal stop 151, likewise moves in the proximal direction P. The first proximal stop 151 is movable relative the inner tubular member 110 to a location proximal to the second distal flow port 422 to expose the first pressure chamber C1 to the second distal flow port 422.

If a third pressure chamber C3 is provided as embodied in FIG. 5, for purpose of example, fluid enters each pressure chamber in tandem, and the operations as described above, within first pressure chamber C1 and second pressure chamber C2 similarly occurs in the third pressure chamber C3. As such, fluid enters the third pressure chamber C3 in tandem as fluid enters the second pressure chamber C2 and the first pressure chamber C1. As fluid enters the third pressure chamber C3, the third proximal seal 352 and the third distal seal 362 seal fluid within the third pressure chamber C3. Once the amount of fluid that enters the third pressure chamber C3 exceeds the initial volume of the third pressure chamber C3, the third pressure chamber C3 pressurizes and an internal force develops within the chamber C3. Since all three pressure chambers C1, C2, and C3 can receive fluid from the same fluid lumen 130, all chambers C1, C2, and C3 will completely fill with fluid and then pressurize before the internal force respectively within each chamber is sufficient to move the outer tubular member 120 in the proximal direction P. For example, if the third pressure chamber C3 and/or the second pressure chamber C2 is filled prior to the first pressure chamber C1, then the fluid entering the fluid lumen will continue to enter the first pressure chamber C1 for balanced pressure within the chambers.

The internal force causes the third proximal seal assembly 350 to engage the third proximal stop 351. In turn, the movable third proximal stop 351 is urged in the proximal direction P in conjunction with the proximal stop 251 and the first proximal stop 151. As the third proximal stop 351 moves in tandem with the second proximal stop 251 and the first proximal stop 251, the outer tubular member 120, being attached to all three stops, likewise is urged in the proximal direction P.

As with the first expansion space X1, the second expansion space X2 will reduce in volume as the second proximal seal assembly 250 moves proximally and the second pressure chamber C2 increases in volume.

As the outer tubular member 120 continues to be urged in the proximal direction P, the first pressure chamber C1 will merge with the first expansion space X1 when the first proximal seal assembly 150 engages the second distal seal assembly 260 and ultimately become exposed to the second distal flow port 422 in addition to the first distal flow port 421. Similarly, the second pressure chamber C2 can merge with the second expansion space X2 when the second proximal seal assembly 250 engages with the third distal seal assembly 360 and ultimately becomes additionally exposed to the third distal flow port 423. In operation, the resulting retraction force generated by the catheter of the disclosed subject matter will be a function of the number of pressurized chambers. For example, each chamber will generally provide a retraction force F, as determined by the pressure within the chamber and the effective surface area at the corresponding seal assembly. Hence, for the catheter of FIG. 4A with two pressure chambers, the resulting force will initially be approximately $2 \times F$. The resulting retraction force therefore will drop to $1 \times F$ when the first pressure chamber C1 merges with the first expansion space X1 and is ultimately exposed to the second distal flow port 422, as shown in FIG. 4C.

Figure 7:
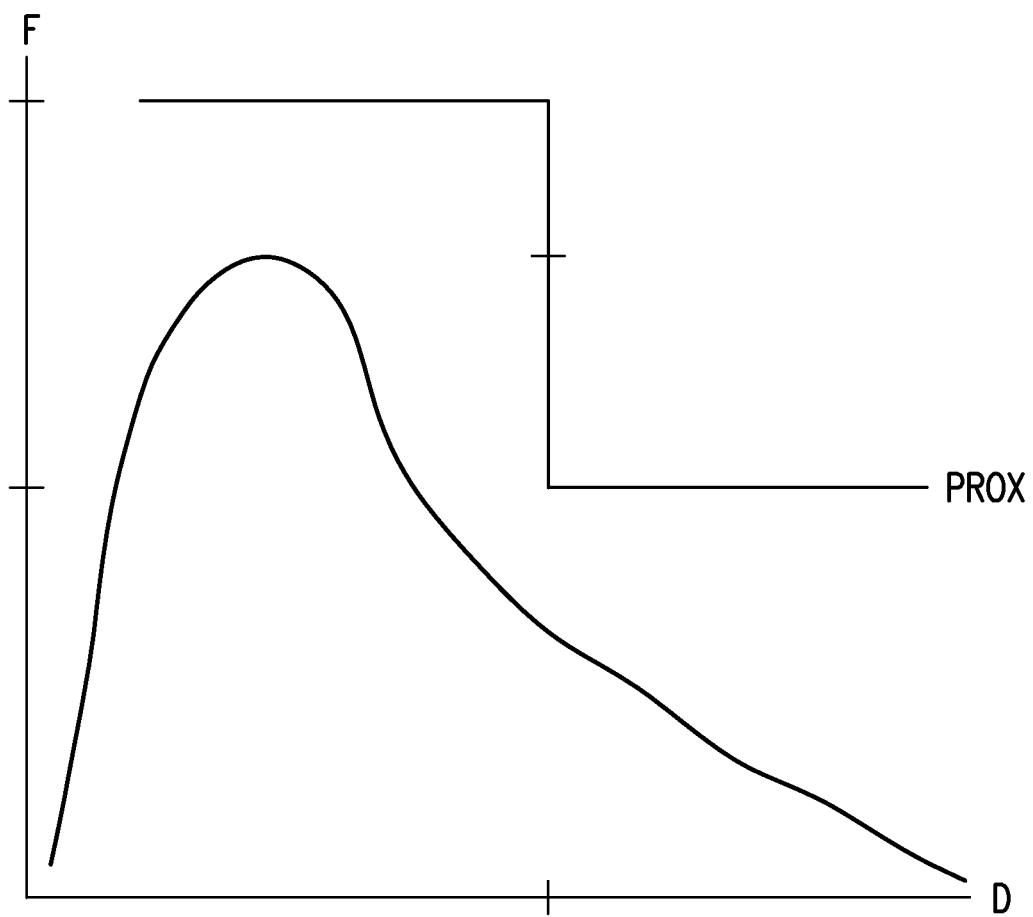
FIG. 7 is a schematic graph of force and distance according to an embodiment of the disclosed subject matter.

The timing for the drop in resulting retraction force therefore can be selected or customized as desired. For example, with the second distal flow port located proximate the second distal seal assembly and the first expansion space having an initial length d1, the resulting force of the catheter embodied in FIG. 4A will drop from approximately $2 \times F$ to approximately $1 \times F$ when the outer tubular member has retracted a distance of about d1. As shown in FIG. 7, the distance d1 can be matched to the distance of retraction required to overcome an initial deployment force.

Similarly, if three chambers are provided, as shown in FIG. 5, the initial resulting force will be approximately $3 \times F$. This force will drop to approximately $2 \times F$ when the first pressure chamber C1 merges with the first expansion space X1 and ultimately is exposed to the second distal flow port 422, and to approximately $1 \times F$ when the first pressure chamber X1 further merges with the second expansion space X2 and is exposed to the third distal flow port 423.

The timing of the first pressure chamber C1 merging with the first expansion space X1 and the second pressure chamber C2 merging with the second expansion space X2 can be configured to occur at the same time or at different times during retraction, and thus at predetermined locations. As noted above, the timing of when each merger occurs will depend upon the distance of each expansion space and location of the corresponding flow port. Hence, the first and second expansion spaces can be provided with different overall lengths for staggered timing of merger. In one embodiment, the most proximal pressure chamber is the longest pressure chamber of the catheter.

In another embodiment, the pressure chambers C1, C2, and C3 and the expansion spaces X1, X2, respectively, have similar dimensions for the pressure chamber to merge within the adjacent expansion space at approximately the same time. As evidenced by FIGS. 4A-4D, the retraction of the outer tubular member 120 causes the stent seat 3 to be exposed and a stent 2 to be released from the inner tubular member 110. The fluid from the pressure chambers can then optionally be withdrawn. If desired, a negative pressure can be drawn in the chambers to lock the outer tubular member in position. The catheter 100 can then be removed from the vasculature as the stent 2 remains released.

Operations of the catheter are further controlled by a suitable indeflator capable of maintaining a selected pressure (not shown). For example, as the outer tubular member is urged in the proximal direction, the indeflator can control the increase in pressure in the chambers to ensure that the outer tubular member is not urged in the proximal direction too abruptly. The indeflator can control the movement of the outer tubular member in the proximal direction. Furthermore, a lock mechanism can be provided to hold a selected pressure or provide only a predetermined volume of fluid to prevent continued retraction.

The number of pressure chambers provided for a catheter and the relative length of the pressure chambers and expansion spaces can be selected or determined based on the length of a stent or device to be deployed. For example, but not limited to, a catheter having two pressure chambers can be provided for a stent ranging approximately between 60 mm and 80 mm. In another embodiment, a catheter having three pressure chambers can be suitable for a stent in excess of 80 mm.

In embodiments of the disclosed subject matter, the inner tubular member and/or outer tubular member can furthermore be manufactured using a variety of known techniques such as but not limited to: extrusion, injection molding, air-blowing, stretching, deep drawing, polymerization, cross-linking, dipping from solution, powder depositioning, sintering, electrospinning, melt spinning, deformation under temperature, stretch blowing, chemical grafting any combination of the above with reinforcement element like metal braids, coils, glass fibers, carbon fibers and other kind of organic or inorganic fibers, liquid crystals, as well as classical machining technologies like heat fusing laser bonding, milling, drilling, grinding, etc. In the event that metallic elements such as hypotubes, are to be incorporated, various metallic manufacturing techniques can be used, such as but not limited to, machining, tube drawing processes, drilling, milling EDM, other deformation methods, plating sputtering, electrografting, sintering, and depositioning e-polishing, among others. In one embodiment of the disclosed subject matter, the inner tubular member includes a stainless steel hypotube at least at its proximal end.

The outer member can be formed of any suitable material or composite that allows expansion. This includes semi-compliant material and expansion materials when the outer member is inflated and/or the pressure chamber is pressurized and retracts when the chamber is depressurized and the outer member is deflated. The outer member can be a single layer, a dual layer, or multilayered and can further be reinforced. For example and not limited thereto, the outer member can be a multilayer tube or balloon including a flexible layer and a rigid layer having a brittle structure configured to fracture upon expansion. The rigid layer can constrain and axially lock a medical device during shipping, storage and delivery, but can rupture upon initial pressurization of the pressure chamber. Once the rigid layer is broken, the flexible layer can maintain a seal while significantly increasing in diameter over the pressure chamber.

Additionally or alternatively, the outer member can have a rigid inner layer and a flexible outer layer, wherein the rigid layer is made of a material that is dissolvable by a selected fluid medium. The pressure chambers can be pressurized with the fluid medium, dissolving the rigid structure and thereby releasing the axial lock and allowing the flexible outer layer to expand in diameter. The outer member can also be formed of a suitable shape-memory material configured to expand across the pressure chamber when the chamber is filled with a hot fluid. As another alternative, the outer member can have a bi-stable design that transitions from a locked or contracted configuration during delivery to an unlocked or expanded configuration upon increased fluid pressure in the pressure chamber.

The outer member can further be provided with an inner layer attached to or formed with an outer layer. The inner layer or liner can include a lubricious material to facilitate the sliding of the outer member in the proximal direction when the outer member is retracted. For example, different types of polymers such as PTFE or high-density polyethylene (HDPE) can be used for the inner layer. Additionally, other lubricious polymers can be used. The outer layer, as embodied herein, provides sufficient strength to capture the intravascular prosthesis therein, as well as allow movement in the proximal direction P. The multiple layers can be formed separately and adhered or bonded together or co-extruded as a single member.

In further accordance with the disclosed subject matter, the outer member can include a reinforcing layer. Solely for purpose of illustration, the reinforcing layer can be disposed at the distal end portion corresponding to the location of the stent seat and disposed between the outer layer and the inner layer, such as a braided or coiled material. For example, the reinforcing layer can be provided in the form of a braided stainless steel tube or sheet or the like. The braid can include flattened filaments, as opposed to having filaments with a round cross-section. Alternatively, the reinforcement can be in the form of a tube including woven fabric or appropriately oriented filaments, such as carbon fibers encased in a polymeric matrix. Likewise, such reinforcing fibers could additionally or alternatively be incorporated into inner layer and/or outer layer during the manufacturing process.

In embodiments where the outer member comprises an inner layer, outer layer and a reinforcing layer, the outer member can be formed in at least the following manner by way of example. First, the inner layer is formed through a tubular extrusion process, and disposed about a forming mandrel. The forming mandrel, as embodied herein, has a shape that corresponds to the desired shape of the inside of the outer member. Next, the reinforcing layer, which can be provided in the form of a stainless steel braid material, is positioned over a predetermined length of inner layer. Next, the outer layer is extruded and positioned over the reinforcing layer. The outer layer can be provided in the form of two separate tubular members that are overlapped slightly at their ends over a reinforcing layer. Each portion of outer layer can be a different material selected to provide a different durometer as described above. The two portions of outer layer can overlap by an amount, such as but not limited to, about 0.1 inches. Next, a sleeve of heat shrinkable material is positioned over the entire outer member assembly. Finally, heat is applied to the assembly. When heat is applied, the heat shrinkable tubing shrinks, and causes the inner layer to fuse with outer layer, trapping the reinforcing layer therebetween. The heating process also causes inner layer to conform to the shape of the forming mandrel. After the assembly cools, the heat shrinkable tubing is cut away, leaving behind the outer member.

As a further alternative, the inner tubular member and/or the outer member can be constructed of multiple outer tubes. The one or more proximal stops can further form a joint for two adjacent outer tubes. The outer member can also be constructed of a composite comprising a fabrication of several different materials, such as a co-extrusion of different polymers, or a fiber-reinforced composite material such as fiber reinforced resin materials or braided materials. Solely for purpose of illustration, further embodiments can include a braided tube with a PTFE liner, a Polyimide middle layer with braiding and a Pebax 72D outer layer. Additionally, to improve flexibility, helical or spiral member configurations can be used in the construction of the inner and outer members.

The inner tubular member and outer tubular member can each be a single piece construction, or an assembly of components, and can be made of any suitable material. For example, suitable materials include, but are not limited to polymer materials such as nylon, urethane, polyurethane, PEEK, PTFE, PVDF, Kynar, PE, HDPE, a trilayer material including L25, Plexar, PEBAX or polyethylene of various suitable densities. Furthermore, at least a portion of the inner tubular member and/or outer tubular member can be constructed of an alloy or metallic material, such as stainless steel hypodermic tubing. Example constructions for the inner member and/or outer tubular member include a single layer of PEEK; a trilayer material of L25, Plexar, HDPE; or a braided tube with a PTFE liner, a Polyimide middle layer with braiding, and a Pebax 72D outer layer.

It is further contemplated that the inner tubular member can be constructed of other biocompatible material. As such, the inner tubular member of the catheter can be constructed from the above-identified polymers, combinations or blends of these polymers, whether alone or in combination with other materials, or other bioabsorbable materials. The inner tubular member can also be reinforced by the addition of a strengthening member, such as, solely for purpose of example, a wire coil. In one embodiment, the inner tubular member is reinforced by the addition of a strengthening member along a length corresponding to the pressure chamber, further described herein.

The inner tubular member and/or outer tubular member can be further coated with any of a variety of materials and techniques to enhance performance if desired, including a number suitable coatings and coating techniques subject to patent matters owned by Abbott Laboratories such as U.S. Pat. Nos. 6,541,116, 6,287,285, and 6,541,116, the entireties of which are hereby incorporated by reference. For example, possible coating materials include lubricious materials such as Teflon®, and hydrophobic materials such as silicone lubricant dispersion PN 4097, or hydrophilic materials such as hydrogel, or lubricious coatings.

The inner tubular member and/or outer tubular member can have any suitable cross-sectional shape, including elliptical, polygon, or prismatic, although a circular cross-section generally is preferred. The inner tubular member and/or outer tubular member can also have any suitable size and diameter depending upon the desired application. The catheter is suitably sized and configured for delivery within a corresponding body lumen for the intended indication, such as a vasculature for vascular intervention.

Additionally, the inner tubular member and/or outer tubular member can be constructed from PE, polypropylene, Kynar, or urethane by an extrusion process using an extruder such as that available any of a number of known suppliers. The materials can be post processed in a number of ways including, for example and not by way of limitation, extrusion, molding, such as by injection or dipping, textile processing such as weaving or braiding, and forming. Forming processes that can be suitable are rolling and welding sheets of material or vacuum forming into tubular shapes, to name only a few examples.

In accordance with another aspect of the disclosed subject matter, the stops can be coextruded or formed with the corresponding inner and outer tubular members or can be formed separately and bonded or otherwise joined to the tubular members. The stops can be constructed of any suitable material, including, but not limited to, PEEK, Pebax, Kynar, and the like.

While the disclosed subject matter is described herein in terms of certain preferred embodiments, those skilled in the art will recognize that various modifications and improvements can be made to the disclosed subject matter without departing from the scope thereof. Additional features known in the art likewise can be incorporated, such as disclosed in U.S. Pat. No. 7,799,065 to Pappas, which is incorporated in its entirety by reference herein. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having any other possible combination of the dependent features claimed below and those disclosed above. Furthermore, the additional features and aspects developed for a single chamber actuator can be incorporated with the tandem chamber catheter disclosed herein, such as disclosed in co-pending application, entitled, "Catheter Having Hydraulic Actuator" and concurrently filed herewith and commonly owned by the Assignee of record. As such, the particular features presented in the dependent claims and disclosed above can be combined with each other in other manners within the scope of the disclosed subject matter such that the disclosed subject matter should be recognized as also specifically directed to other embodiments having any other possible combinations. Furthermore, although reference is made to a stent throughout this disclosure, other suitable devices and implants likewise can be delivered using the catheter and system disclosed herein. Thus, the foregoing description of specific embodiments of the disclosed subject matter has been presented for purposes of illustration and description. It is not intended to be exhaustive or to limit the disclosed subject matter to those embodiments disclosed.

Many modifications, variations, or other equivalents to the specific embodiments described above will be apparent to those familiar with the art. It is intended that the scope of this disclosed subject matter be defined by the claims below and those modifications, variations and equivalents apparent to practitioners familiar with this art.

What is claimed is:

1. A catheter, comprising:
   an inner tubular member having a length, an exterior surface and a fluid lumen defined therein, the exterior surface defining a first distal flow port in fluid communication with the fluid lumen and a second distal flow port located proximal to the first distal flow port in fluid communication with the fluid lumen;
   an outer tubular member movable relative to the inner tubular member in a proximal direction along a length of the inner tubular member, the outer tubular member having an interior surface directed toward the exterior surface of the inner tubular member;
   a first pressure chamber defined between the exterior surface of the inner tubular member and the interior surface of the outer tubular member, and between a first distal seal assembly and a first proximal seal assembly, the first pressure chamber in fluid communication with the first distal flow port; and
   a second pressure chamber defined between the exterior surface of the inner tubular member and the interior surface of the outer tubular member, and between a second distal seal assembly and a second proximal seal assembly, the second pressure chamber disposed proximal to the first pressure chamber and in fluid communication with the second distal flow port;
   wherein fluid introduced through the fluid lumen pressurizes the first pressure chamber and the second pressure chamber to generate a respective force at the first proximal seal assembly and the second proximal seal assembly to urge the outer tubular member in the proximal direction.

2. The catheter according to claim 1, wherein the first distal seal assembly includes a first distal stop and a first distal seal, the first distal stop extending from the exterior surface of the inner tubular member toward the interior surface of the outer member and disposed distal to the first distal seal to inhibit movement of the first distal seal in a distal direction, and further wherein the first proximal seal assembly includes a first proximal stop and a first proximal seal, the first proximal stop extending from the interior surface of the outer tubular member and disposed proximal to the first proximal seal, the first proximal stop being movable relative the inner tubular member in the proximal direction.

3. The catheter according to claim 2, wherein at least one of the first distal seal assembly or the second distal seal assembly further includes a bushing.

4. The catheter according to claim 2, wherein the second distal seal assembly includes a second distal stop and a second distal seal, the second distal stop extending from the exterior surface of the inner tubular member and disposed distal to the second distal seal to inhibit movement of the second distal seal in a distal direction, and further wherein the second proximal seal assembly includes a second proximal stop and a second proximal seal, the second proximal stop extending from the interior surface of the outer tubular member and disposed proximal to the second proximal seal, the second proximal stop being movable relative the inner tubular member in the proximal direction.

5. The catheter according to claim 4, wherein the first proximal seal engages the first proximal stop and the second proximal seal engages the second proximal stop when the first pressure chamber and the second pressure chambers are pressurized, respectively, to urge the outer tubular member in the proximal direction.

6. The catheter according to claim 4, wherein the first proximal stop is movable relative the inner tubular member to a location proximal the second distal flow port to expose the first pressure chamber to the second distal flow port.

7. The catheter according to claim 1, wherein the exterior surface of the inner tubular member further defines a third distal flow port proximal to the second distal flow port, the third distal flow port in fluid communication with the fluid lumen; and wherein the catheter further comprises a third pressure chamber in fluid communication with the third distal flow port of the fluid lumen, the third pressure chamber defined between the exterior surface of the inner tubular member, the interior surface of the outer tubular member, a third proximal seal assembly, and a third distal seal assembly, wherein fluid introduced through the fluid lumen pressurizes the third pressure chamber in tandem with the first pressure chamber and the second pressure chamber to apply a force to the third proximal seal assembly to urge the outer tubular member in the proximal direction.

8. The catheter according to claim 7, wherein the third distal seal assembly includes a third distal stop and a third distal seal, the third distal stop extending from the exterior surface of the inner tubular member and disposed distal to the third distal seal to inhibit movement of the third distal seal in the distal direction, and further wherein the third proximal seal assembly includes a third proximal stop and a third proximal seal, the third proximal stop extending from the interior surface of the outer tubular member and disposed proximal to the third proximal seal, the third proximal stop being movable relative the inner tubular member in the proximal direction.

9. The catheter according to claim 1, wherein the inner tubular member further has a guidewire lumen defined therein.

10. The catheter according to claim 9, wherein the guidewire lumen has a proximal guidewire port spaced distal to a proximal end of the catheter.

11. The catheter according to claim 9, further comprising a guidewire tube disposed within the fluid lumen to define the guidewire lumen.

12. The catheter according to claim 9, wherein the guidewire lumen is defined in the fluid lumen, the inner tubular member further comprising a proximal guidewire seal and a distal guidewire seal disposed in the fluid lumen to sealingly engage a guidewire disposed within the fluid lumen.

13. The catheter according to claim 12, wherein at least one of the proximal guidewire seal or the distal guidewire seal is formed of at least one of hydrophilic material, hydrophobic material, or molded hydrophilic material.

14. The catheter according to claim 3, wherein at least one of the first distal seal, the first proximal seal, the second distal seal, or the second proximal seal is formed of at least one of hydrophilic material, hydrophobic material, or molded hydrophilic material.

15. The catheter according to claim 1, further comprising a radiopaque marker secured to the inner tubular member.

16. The catheter according to claim 15, wherein the radiopaque marker seals the fluid lumen distal to the first distal flow port.

17. The catheter according to claim 1, further comprising a strengthening member coupled along a portion of the inner tubular member corresponding to at least one of the first pressure chamber or the second pressure chamber.

18. The catheter according to claim 1, further comprising a stent seat disposed along the inner tubular member distal to the first pressure chamber and a stent positioned at the stent seat.

19. The catheter according to claim 18, wherein the outer tubular member is coextensive with the stent seat in a first position, and movement of the outer tubular member in the proximal direction to a second position to deploy the stent.

20. The catheter according to claim 1, wherein the outer tubular member is formed of a shape memory material, the outer sheath being radially expandable upon increased fluid temperature in the pressure chamber.

21. The catheter according to claim 1, wherein the outer tubular member comprises a multi-layered configuration.

22. The catheter according to claim 1, further comprising a first expansion space defined between the exterior surface of the inner tubular member and the interior surface of the outer tubular member and between the first pressure chamber and the second pressure chamber, the first expansion space configured to reduce in volume as the first pressure chamber increases in volume.

23. The catheter according to claim 22, wherein the first expansion space is filled initially with a compressible fluid.

24. The catheter according to claim 22, wherein the first pressure chamber merges with the first expansion space when the outer tubular member moves a predetermined distance in the proximal direction.

25. The catheter according to claim 23, wherein the first pressure chamber is exposed to the second distal flow port when the outer tubular member is moved the predetermined distance in the proximal direction.

26. The catheter according to claim 23, wherein the first pressure chamber generates a continued retracting to urge the outer tubular member in the proximal direction beyond the predetermined distance.

27. The catheter according to claim 1, wherein the first pressure chamber and the second pressure chamber collectively generate an initial resulting retraction force to urge the outer tubular member initially in the proximal direction.

28. The catheter according to claim 7, further comprising a first expansion space between the first pressure chamber and the second pressure chamber, and second expansion space positioned between the second pressure chamber and the third pressure chamber.

29. The catheter according to claim 4, wherein the first proximal seal assembly moves proximal to the second distal stop in the proximal direction to expose the first pressure chamber to the second distal flow port.

30. The catheter according to claim 4, wherein the second distal stop is formed at least in part by a bump, platform, sleeve, raiser, or step.

31. The catheter according to claim 30, wherein the bump has a wedge or conical configuration.

32. The catheter according to claim 1, further comprising an indeflator for fluid communication within the fluid lumen.

33. A method of deploying a catheter, comprising:
providing a catheter including:
an inner tubular member having a length, an exterior surface and a fluid lumen defined therein, the exterior surface defining a first distal flow port in fluid communication with the fluid lumen and a second distal flow port located proximal to the first distal flow port in fluid communication with the fluid lumen,
an outer tubular member movable relative to the inner tubular member in a proximal direction along a length of the inner tubular member, the outer tubular member having an interior surface directed toward the exterior surface of the inner tubular member, a first pressure chamber defined between the exterior surface of the inner tubular member and the interior surface of the outer tubular member, and between a first distal seal assembly and a first proximal seal assembly, the first pressure chamber in fluid communication with the first distal flow port, and a second pressure chamber defined between the exterior surface of the inner tubular member and the interior surface of the outer tubular member, and between a second distal seal assembly and a second proximal seal assembly, the second pressure chamber disposed proximal to the first pressure chamber and in fluid communication with the second distal flow port;

disposing a device between the exterior surface of the inner tubular member and the interior surface of the outer tubular member at a location distal to the first distal seal assembly; and introducing fluid into the fluid lumen to pressurize the first pressure chamber and the second pressure chamber to generate a respective force at the first proximal seal assembly and the second proximal seal assembly to move the outer tubular member in the proximal direction to expose the device.

* * * * *